(12) United States Patent
Banner et al.

(10) Patent No.: US 7,612,099 B2
(45) Date of Patent: Nov. 3, 2009

(54) VINYLOGOUS ACID DERIVATIVES

(75) Inventors: David Banner, Basel (CH); Hans Hilpert, Muenchenstein (CH); Bernd Kuhn, Liestal (CH); Harald Mauser, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 394 days.

(21) Appl. No.: 11/605,016

(22) Filed: Nov. 28, 2006

(65) Prior Publication Data

US 2007/0129421 A1    Jun. 7, 2007

(30) Foreign Application Priority Data

Dec. 1, 2005    (EP)    ................... 05111598

(51) Int. Cl.
```
A61K 31/4439    (2006.01)
A61K 31/4178    (2006.01)
A61K 31/404     (2006.01)
C07D 403/06     (2006.01)
C07D 401/06     (2006.01)
C07D 209/08     (2006.01)
C07D 209/32     (2006.01)
C07D 209/04     (2006.01)
```
(52) U.S. Cl. ................ 514/339; 514/397; 514/413; 514/414; 514/415; 546/277.4; 548/312.1; 548/455; 548/465

(58) Field of Classification Search .............. 514/339, 514/397, 413, 414, 415; 548/312.1, 455, 548/465; 546/277.4
See application file for complete search history.

(56) References Cited

U.S. PATENT DOCUMENTS

| | | | |
|---|---|---|---|
| 4,443,615 | A | 4/1984 | Matsuoka et al. |
| 5,436,264 | A | 7/1995 | Pfister et al. |
| 6,432,978 | B1 | 8/2002 | Tani et al. |
| 6,852,734 | B2 * | 2/2005 | Yamamoto et al. .......... 514/312 |
| 2005/0119329 | A1 | 6/2005 | Godel et al. |

FOREIGN PATENT DOCUMENTS

| | | |
|---|---|---|
| EP | 1284266 | 2/1993 |
| EP | 701988 | 3/1996 |
| EP | 945443 | 9/1999 |
| EP | 1136488 | 9/2001 |
| JP | 05078250 | 3/1993 |
| WO | WO 8200032 | 2/1982 |
| WO | WO 93/23040 | 11/1993 |
| WO | WO 93/23041 | 11/1993 |
| WO | WO 00/35452 | 6/2000 |
| WO | WO 03016307 | 2/2003 |
| WO | WO 2004/082687 | 9/2004 |
| WO | WO 2005/009993 | 2/2005 |

OTHER PUBLICATIONS

Doggrell et al., Can. J. Physiol. Pharmacol., 83, pp. 123-130 (2005).
Lindstedt et al., Curr. Opin. Lipidol, 15, pp. 567-573 (2004).
Reed et al., J. Allergy Clin. Immunol., 114, pp. 997-1008 (2004).
Takai et al., Eur. J. Pharmacol, 501, pp. 1-8 (2004).
Takai etal., Trends Pharmacol Sci., 25(10), pp. 518-522 (2004).
Miyata et al., Angew. Chem., 94(8), pp. 651-652 (1982).
Hofheinz et al., Helvetica Chimica Acta, 60(2), pp. 660-669 (1977).
Galeotti et al., J. Org. Chem., 58, pp. 5370-5376 (1993).
Krepski et al., Tetrahedron Letters, 26(8), pp. 981-984 (1985).
Compain et al., Synlett, 11, pp. 943-945 (1994).
Nguyen et al., J. Am. Chem. Soc., 125, pp. 11818-11819 (2003).
Hamer, N.K., Tetrahedron Letters, 27(19), pp. 2167-2168 (1986).
Matsuo et al., Chem. Pharm. Bull., 32(9), pp. 3724-3729 (1984).
Mizuno et al., Chem. Pharm. Bull., 23(3), pp. 527-537 (1975).
Ho et al., J. Medicinal Chemistry, 14(6), pp. 553-554 (1971).
Hasegawa et al., Heterocycles, 51(12), pp. 2815-2821 (1999).
Contour-Galcéra et al., Bioorganic & Medicinal Chemistry Letters, 15, pp. 3555-3559 (2005).
Khalil et al., Journal of Biological Chemistry, 273(46), pp. 30321-30327(1998).
Nenajdenko et al., Tetrahedron, 60, pp. 11719-11724 (2004).
Cheve et al., Med. Chem. Res., 11(7), pp. 361-379 (2003).
Mor et al., J. Med. Chem., 41, pp. 3831-3844 (1998).
Heath-Brown et al., J. Chem. Soc., Abstracts, pp. 7165-7178 (1965).
Nagarathnam et al., Synthetic Communications, 23(14), pp. 2011-2017 (1993).
Hengartner et al., J. Org. Chem., 44(22), pp. 3741-3747 (1979).
Yang et al., Indian Journal of Chemistry, 38B(8), pp. 897-904 (1999).
Tani, M. et al, Jour. of Antibiotics, 57(2) 89-96 (2004) XP002419474.
Tani, M. et al, Jour. of Antibiotics, 57(2) 83-88 (2004) XP002419475.

* cited by examiner

Primary Examiner—Rebecca L Anderson
Assistant Examiner—Jason Nolan
(74) Attorney, Agent, or Firm—George W. Johnston; Dennis P. Tramaloni; Brian C. Remy

(57) ABSTRACT

The invention is concerned with vinylogous acids derivatives of formula (I)

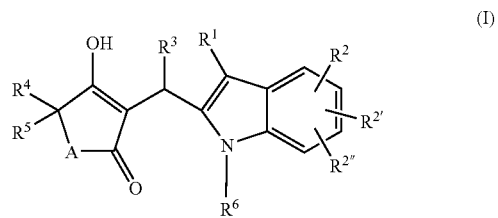

wherein A and $R^1$ to $R^6$ are as defined in the description and in the claims, as well as physiologically acceptable salts thereof. These compounds inhibit chymase and can be used as medicaments.

23 Claims, No Drawings

VINYLOGOUS ACID DERIVATIVES

PRIORITY TO RELATED APPLICATIONS

This application claims the benefit of European Application No. 05111598.8 filed Dec. 1, 2005, which is hereby incorporated by reference in its entirety.

The invention is concerned with novel vinylogous acid derivatives of formula (I),

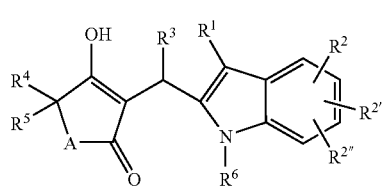

wherein

A is —CH$_2$—, —O— or —NR'—, in which R' is hydrogen or C$_{1-6}$ alkyl, or wherein R' and R$^4$ form C$_{2-5}$ alkylene;

R$^1$ is hydrogen, halogen, nitro, cyano, amino, C$_{1-6}$ alkyl, heteroalkyl, C$_{3-7}$ cycloalkyl, C$_{2-6}$ alkenyl, C$_{2-6}$ alkynyl, hydroxy, C$_{1-6}$ alkoxy, —NR'R", —(C$_{0-6}$ alkylene)-NR'R", in which R' and R" are independently selected from the group consisting of hydrogen, C$_{1-6}$ alkyl, heteroalkyl, formyl, C$_{1-6}$ alkylcarbonyl, optionally substituted C$_{3-7}$ cycloalkylcarbonyl, optionally substituted arylcarbonyl, optionally substituted heteroarylcarbonyl, optionally substituted heterocyclylcarbonyl, C$_{1-6}$ alkylsulfonyl, optionally substituted C$_{3-7}$ cycloalkylsulfonyl, optionally substituted arylsulfonyl, optionally substituted heteroarylsulfonyl and optionally substituted heterocyclylsulfonyl, or —(C$_{0-6}$ alkylene)-OR', in which R' is hydrogen, C$_{1-6}$ alkyl, heteroalkyl, formyl or C$_{1-6}$ alkylcarbonyl;

R$^2$, R$^{2'}$ and R$^{2''}$ are independently hydrogen, halogen, cyano, nitro, amino, mono- or di-C$_{1-6}$alkyl substituted amino, C$_{1-6}$ alkyl, C$_{2-6}$ alkenyl, C$_{2-6}$ alkynyl, heteroalkyl, hydroxy or C$_{1-6}$ alkoxy;

R$^3$ is hydrogen, halogen, cyano, nitro, amino, mono- or di-C$_{1-6}$ alkyl substituted amino, C$_{1-6}$ alkyl, C$_{2-6}$ alkenyl, C$_{2-6}$ alkynyl, heteroalkyl, hydroxy, C$_{1-6}$ alkoxy, optionally substituted C$_{3-7}$ cycloalkyl, optionally substituted aryl, optionally substituted heteroaryl, optionally substituted heterocyclyl, optionally substituted C$_{3-7}$ cycloalkyl-C$_{1-6}$ alkyl, optionally substituted aryl-C$_{1-6}$ alkyl, optionally substituted heteroaryl-C$_{1-6}$ alkyl or optionally substituted heterocyclyl-C$_{1-6}$ alkyl;

R$^4$ is hydrogen, halogen, cyano, nitro, amino, mono- or di-C$_{1-6}$ alkyl substituted amino, C$_{1-6}$ alkyl, C$_{2-6}$ alkenyl, C$_{2-6}$ alkynyl, heteroalkyl, hydroxy, C$_{1-6}$ alkoxy, optionally substituted C$_{3-7}$ cycloalkyl, optionally substituted aryl, optionally substituted heteroaryl, optionally substituted heterocyclyl, optionally substituted C$_{3-7}$ cycloalkyl-C$_{1-6}$ alkyl, optionally substituted aryl-C$_{1-6}$ alkyl, optionally substituted heteroaryl-C$_{1-6}$ alkyl or optionally substituted heterocyclyl-C$_{1-6}$ alkyl;

R$^5$ is hydrogen or C$_{1-6}$ alkyl; or

R$^4$ and R$^5$, together with the carbon atom to which they are attached, form optionally substituted C$_{3-7}$ cydoalkyl ring or optionally substituted heterocyclyl ring;

R$^6$ is hydrogen or C$_{1-6}$ alkyl;

and prodrugs and pharmaceutically acceptable salts thereof.

Further, the invention is concerned with a process and an intermediate for the manufacture of the above compounds, pharmaceutical preparations which contain such compounds, the use of these compounds for the production of pharmaceutical preparations as well as a process for the manufacture of the intermediate.

The compounds of formula (I) inhibit chymase. Chymase is a serine proteinase with an expression pattern strictly limited to a sub-population of mast cells (M$_{CT}$mast cell). Chymase is activated only upon mast cell activation and degranulation, which restricts the enzyme activity to M$_{CT}$ positive tissues. Chymase specifically cleaves a number of pathologically relevant substrates whereby it can activate angiotensin II, endothelin, TGFb, Il1, SCF, collagenase and degrade proteins like thrombin, FN, APO A1.2. This pattern renders chymase an attractive target for allergic, inflammatory and fibrotic diseases. Indeed, a number of successful animal studies with chymase inhibitors have demonstrated efficacy in atopic animals, vascular injury and atherosclerosis.

Thus inhibition of chymase appears a useful modality in the treatment of allergy, asthma, peripheral arterial occlusive disease, critical limb ischemia, vulnerable atherosclerotic plaque patients, unstable angina, congestive heart failure, left ventricular hypertrophy, ischemia reperfusion injury, cardiomyopathy, restenosis, rheumatoid arthritis, diabetic nephropathy, irritable bowel disease, Crohn's disease, and wound healing (burns/ulcers in Diabetes/CLI).

The present invention provides the novel compounds of formula (I) which are chymase inhibitors.

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and fluorine being preferred.

The term "C$_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. C$_{1-4}$ alkyl is more preferred.

The term "heteroalkyl" means C$_{1-6}$ alkyl substituted by one or more substituents selected independently from the group consisting of nitro, hydroxy, halogen, cyano, C$_{1-6}$ alkoxy, formyl, C$_{1-6}$ alkylcarbonyl, carboxyl, C$_{1-6}$ alkylthio, C$_{1-6}$ alkyl sulfinyl, C$_{1-6}$ alkyl sulfonyl, amino and mono- or di-C$_{1-6}$ alkyl substituted amino. This term is further exemplified by such radicals as 2-hydroxyethyl, perfluoromethyl. C$_{1-6}$ alkyl substituted by one hydroxy group or one to three same or different halogen atoms are preferred.

The term "C$_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "C$_{1-6}$ alkoxy", alone or in combination with other groups, means the group R'—O—, wherein R' is a C$_{1-6}$ alkyl.

The term "C$_{2-6}$ alkenyl", alone or in combination with other groups, means a straight-chain or branched hydrocarbon residue comprising an olefinic bond, having two to six carbon atoms, such as ethenyl and 2-propenyl.

The term "C$_{2-6}$-alkynyl", alone or in combination with other groups, means a straight-chain or branched hydrocarbon residue comprising a triple bond, having two to six carbon atoms, such as ethynyl and 2-propynyl.

The term "C$_{0-6}$ alkylene" means a bond or a straight chain or branched divalent saturated aliphatic hydrocarbon group of 1 to 6 carbon atoms. C$_0$ alkylene means a bond.

The term "aryl", alone or in combination with other groups, means a phenyl or a naphthyl group, preferably a phenyl group.

The term "heterocyclyl", alone or combination with other groups, means non-aromatic mono- or bi-cyclic radicals of three to eight ring atoms in which one or two ring atoms are heteroatoms selected from N, O, or $S(O)_n$ (where n is an integer from 0 to 2), the remaining ring atoms being C.

The term "heteroaryl" means a monocyclic or bicyclic radical of 5 to 12 ring atoms having at least one aromatic ring containing one, two, or three ring heteroatoms selected from N, O, and S, the remaining ring atoms being C. Preferably, the attachment point of the heteroaryl radical will be on an aromatic ring.

The term "optionally substituted aryl", "optionally substituted heteroaryl", "optionally substituted heterocyclyl" and "optionally substituted $C_{3-7}$ cycloalkyl" means, respectively aryl, heteroaryl, heterocyclyl and $C_{3-7}$ cycloalkyl optionally substituted by one or more substituents independently selected from the group consisting of halogen, nitro, cyano, amino, $C_{1-6}$ alkyl, $C_{2-6}$ alkenyl, $C_{2-6}$ alkynyl, hydroxy, $C_{1-6}$ alkoxy, mono- or di-$C_{1-6}$ alkyl substituted amino and heteroalkyl.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na-, K-, Ca- and trimethylammonium salts. The term "pharmaceutically acceptable salts" also refers to such salts. Acid addition salts as described above are preferred.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) A preferred compound of the invention is a compound of formula (I), wherein $R^3$ is $C_{1-6}$ alkyl, optionally substituted aryl, optionally substituted heteroaryl, optionally substituted aryl $C_{1-6}$ alkyl or optionally substituted heteroaryl $C_{1-6}$ alkyl.

ii) Another preferred compound of the invention is a compound of formula (I), wherein $R^3$ is $C_{1-6}$ alkyl; phenyl $C_{1-6}$ alkyl; phenyl optionally substituted by one to three fluorine atoms; or heteroaryl optionally substituted by one to three fluorine atoms, in which heteroaryl is a monocyclic aromatic radical of 5 or 6 ring atoms, containing one or two ring nitrogen atoms or one ring sulfur atom.

iii) Another preferred compound of the invention is a compound of formula (I), wherein $R^3$ is phenyl.

iv) Another preferred compound of the invention is a compound of formula (I), wherein $R^1$ is $C_{1-6}$ alkyl, —$(C_{0-6}$ alkylene)-NR'R", in which R' and R" are independently selected from the group consisting of hydrogen, $C_{1-6}$ alkylcarbonyl, optionally substituted arylcarbonyl, optionally substituted heteroarylcarbonyl, optionally substituted arylsulfonyl and optionally substituted heteroarylsulfonyl or —$(C_{0-6}$ alkylene)-OR', in which R' is hydrogen or $C_{1-6}$ alkylcarbonyl.

v) Another preferred compound of the invention is a compound of formula (I), wherein $R^1$ is $C_{1-6}$ alkyl, —$(C_{2-6}$ alkylene)-NR'R", in which R' and R" are independently selected from the group consisting of hydrogen, acetyl, arylcarbonyl, in which aryl is optionally substituted by one or two trifluoromethyl groups, and arylsulfonyl or —$(C_{2-6}$ alkylene)-OR', in which R' is hydrogen or acetyl.

vi) Another preferred compound of the invention is a compound of formula (I), wherein $R^1$ is 2-aminoethyl, 2-acetylaminoethyl, 2-acetylamino-2,2-dimethylethyl, methyl, isopropyl or 2-hydroxyethyl.

vii) Another preferred compound of the invention is a compound of formula (I), wherein $R^2$, $R^{2'}$ and $R^{2''}$ are independently hydrogen, halogen, $C_{1-6}$ alkyl or $C_{1-6}$ alkoxy.

viii) Another preferred compound of the invention is a compound of formula (I), wherein two of $R^2$, $R^{2'}$ and $R^{2''}$ are hydrogen, and the other is hydrogen, halogen, $C_{1-6}$ alkyl or $C_{1-6}$ alkoxy.

ix) Another preferred compound of the invention is a compound of formula (I), wherein two of $R^2$, $R^{2'}$ and $R^{2''}$ are hydrogen, and the other is hydrogen, chloro, fluoro, methyl, ethyl or methoxy.

x) Another preferred compound of the invention is a compound of formula (I), wherein two of $R^2$, $R^{2'}$ and $R^{2''}$ are hydrogen, and the other is at 5 or 6 position of the indole ring and selected from the group consisting of hydrogen, chloro, fluoro, methyl and ethyl.

xi) Another preferred compound of the invention is a compound of formula (I), wherein $R^6$ is hydrogen.

xii) Another preferred compound of the invention is a compound of formula (I), wherein $R^4$ is hydrogen, $C_{1-6}$ alkyl, optionally substituted $C_{3-7}$ cycloalkyl, optionally substituted aryl, optionally substituted $C_{3-7}$ cycloalkyl $C_{1-6}$ alkyl or optionally substituted aryl $C_{1-6}$ alkyl and Rhu 5 is hydrogen or $C_{1-6}$ alkyl; or $R^4$ and $R^5$, together with the carbon atom to which they are attached, form an optionally substituted $C_{3-7}$ cycloalkyl ring.

xiii) Another preferred compound of the invention is a compound of formula (I), wherein A is —$CH_2$—.

xiv) Another preferred compound of the invention is a compound of formula (I), wherein A is —$CH_2$—, $R^4$ is phenyl and $R^5$ is hydrogen.

xv) Another preferred compound of the invention is a compound of formula (I), wherein A is —NR'—, in which R' is hydrogen or $C_{1-6}$ alkyl.

xvi) Another preferred compound of the invention is a compound of formula (I), wherein A is —NR'—, in which R' is hydrogen or methyl, $R^4$ is isopropyl and $R^5$ is hydrogen.

xvii) Another preferred compound of the invention is a compound of formula (I), wherein A is —O—.

xviii) Another preferred compound of the invention is a compound of formula (I), wherein A is —O—, $R^4$ is hydrogen, phenyl, $C_{1-6}$ alkyl, optionally substituted $C_{3-7}$ cycloalkyl $C_{1-6}$ alkyl or optionally substituted aryl $C_{1-6}$ alkyl and $R^5$ is hydrogen or $C_{1-6}$ alkyl; or $R^4$ and $R^5$, together with the carbon atom to which they are attached, form optionally substituted $C_{3-7}$ cycloalkyl ring.

xix) Another preferred compound of the invention is a compound of formula (I), wherein A is —O—, $R^4$ is phenyl, benzyl, isobutyl, 2-cyclohexylethyl or phenethyl and $R^5$ is hydrogen or methyl.

xx) Another preferred compound of the invention is a compound of formula (I), wherein $R^3$ is $C_{1-6}$ alkyl, optionally substituted aryl, optionally substituted heteroaryl, optionally substituted aryl $C_{1-6}$ alkyl or optionally substituted heteroaryl $C_{1-6}$ alkyl, preferably $R^3$ is $C_{1-6}$ alkyl, phenyl optionally substituted by one to three fluorine atoms, heteroaryl optionally substituted by one to three fluorine atoms, in which heteroaryl is a monocyclic aromatic radical of 5 or 6 ring atoms, containing one or two ring nitrogen atoms, or phenyl $C_{1-6}$ alkyl, especially phenyl;

$R^1$ is $C_{1-6}$ alkyl, —$(C_{0-6}$ alkylene)-NR'R", in which R' and R" are independently selected from the group consisting of hydrogen, $C_{1-6}$ alkylcarbonyl, optionally substituted arylcarbonyl, optionally substituted heteroarylcarbonyl, optionally substituted arylsulfonyl and optionally substituted heteroarylsulfonyl or —$(C_{0-6}$ alkylene)-OR', in which R' is hydrogen or $C_{1-6}$ alkylcarbonyl, preferably R' is $C_{1-6}$ alkyl, —$(C_{2-6}$ alkylene)-NR'R", in which R' and R" are independently selected from the group consisting of hydrogen, acetyl, arylcarbonyl, in which aryl is optionally substituted by one or two perfluoro methyl and arylsulfonyl or —$(C_{2-6}$ alkylene)-OR', in which R' is hydrogen or acetyl, especially 2-aminoethyl, 2-acetylaminoethyl, 2-acetylamino-2,2-dimethylethyl, methyl, isopropyl or 2-hydroxyethyl;

$R^2$, $R^{2'}$ and $R^{2''}$ are independently hydrogen, halogen, $C_{1-6}$ alkyl or $C_{1-6}$ alkoxy, preferably two of $R^2$, $R^{2'}$ and $R^{2''}$ are hydrogen, and the other is hydrogen, halogen, $C_{1-6}$ alkyl or $C_{1-6}$ alkoxy, more preferably two of $R^2$, $R^{2'}$ and $R^{2''}$ are hydrogen, and the other is hydrogen, chloro, fluoro, methyl, ethyl or methoxy, especially two of $R^2$, $R^{2'}$ and $R^{2''}$ are hydrogen, and the other is at 5 or 6 position of the indole ring and selected from the group consisting of hydrogen, chloro, fluoro, methyl and ethyl;

$R^6$ is hydrogen;

$R^4$ is hydrogen, $C_{1-6}$ alkyl, optionally substituted $C_{3-7}$ cycloalkyl, optionally substituted aryl, optionally substituted $C_{3-7}$ cycloalkyl $C_{1-6}$ alkyl or optionally substituted aryl $C_{1-6}$ alkyl;

$R^5$ is hydrogen or $C_{1-6}$ alkyl; or $R^4$ and $R^5$, together with the carbon atom to which they are attached, form optionally substituted $C_{3-7}$ cycloalkyl ring.

xxi) A preferred compound of group xx) is a compound of formula (I), wherein A is —$CH_2$—. When A is —$CH_2$—, preferably $R^4$ is phenyl and $R^5$ is hydrogen.

xxii) Another preferred compound of group xx) is a compound of formula (I), wherein A is —NR'—, in which R' is hydrogen or $C_{1-6}$ alkyl, preferably hydrogen or methyl. When A is —NR'—, in which R' is hydrogen or methyl, preferably $R^4$ is isopropyl and $R^5$ is hydrogen.

xxiii) Another preferred compound of group xx) is a compound of formula (I), wherein A is —O—. When A is —O—, preferably $R^4$ is hydrogen, phenyl, $C_{1-6}$ alkyl, optionally substituted $C_{3-7}$ cycloalkyl $C_{1-6}$ alkyl or optionally substituted aryl $C_{1-6}$ alkyl and $R^5$ is hydrogen or $C_{1-6}$ alkyl; or $R^4$ and $R^5$, together with the carbon atom to which they are attached, form optionally substituted $C_{3-7}$ cycloalkyl ring.

When A is —O—, more preferably $R^4$ is phenyl, benzyl, isobutyl, 2-cyclohexylethyl or phenethyl and $R^5$ is hydrogen or methyl.

xxiv) Another preferred compound of the invention is a compound of formula (I), wherein A is —$CH_2$—, —O— or —NR'—, in which R' is hydrogen or $C_{1-6}$ alkyl.

xxv) Another preferred compound of the invention is a compound of formula (I), wherein A is —NR'—, in which R' and $R^4$ form $C_{2-5}$ alkylene.

xxvi) Another preferred compound of the invention is a compound of formula (I), which is 3-[(5-Fluoro-3-methyl-1H-indol-2-yl)-phenyl-methyl]-4-hydroxy-5-isopropyl-1,5-dihydro-pyrrol-2-one, 3-[(5-Fluoro-3-methyl-1H-indol-2-yl)-phenyl-methyl]-4-hydroxy-5-isopropyl-1-methyl-1,5-dihydro-pyrrol-2-one, 4-Hydroxy-5-isopropyl-3-[(3-methyl-1H-indol-2-yl)-phenyl-methyl]-1,5-dihydro-pyrrol-2-one, 3-[(5-Fluoro-3-isopropyl-1H-indol-2-yl)-phenyl-methyl]-4-hydroxy-5-isopropyl-1,5-dihydro-pyrrol-2-one, N-(2-{2-[(5-Benzyl-4-hydroxy-2-oxo-2,5-dihydro-furan-3-yl)-phenyl-methyl]-6-fluoro-1H-indol-3-yl}-ethyl)-acetamide, 5-Benzyl-3-{[6-fluoro-3-(2-hydroxy-ethyl)-1H-indol-2-yl]-phenyl-methyl}-4-hydroxy-5H-furan-2-one, 3-{[3-(2-Amino-ethyl)-6-fluoro-1H-indol-2-yl]-phenyl-methyl}-5-benzyl-4-hydroxy-5H-furan-2-one; salt with acetic acid, 5-Benzyl-3-[(5-fluoro-3-methyl-1H-indol-2-yl)-phenyl-methyl]-4-hydroxy-5H-furan-2-one, (2-{6-Fluoro-2-[(4-hydroxy-5-methyl-2-oxo-5-phenyl-2,5-dihydro-furan-3-yl)-phenyl-methyl]-indol-3-yl}-ethyl)-acetamide, (2-{2-[(4-Hydroxy-5-isobutyl-2-oxo-2,5-dihydro-furan-3-yl)-phenyl-methyl]-indol-3-yl}-ethyl)-acetamide, N-[2-(2-{[5-(2-Cyclohexyl-ethyl)-4-hydroxy-2-oxo-2,5-dihydro-furan-3-yl]-phenyl-methyl}-6-fluoro-1H-indol-3-yl)-ethyl]-acetamide, N-(2-{6-Fluoro-2-[(4-hydroxy-2-oxo-5-phenethyl-2,5-dihydro-furan-3-yl)-phenyl-methyl]-1H-indol-3-yl}-ethyl)-acetamide, N-(2-{2-[(2-Hydroxy-5-oxo-3-phenyl-cyclopent-1-enyl)-phenyl-methyl]-1H-indol-3-yl}-ethyl)-acetamide, N-(2-{6-Fluoro-2-[(2-hydroxy-5-oxo-3-phenyl-cyclopent-1-enyl)-phenyl-methyl]-1H-indol-3-yl}-ethyl)-acetamide, N-(2-{5-Ethyl-2-[(2-hydroxy-5-oxo-3-phenyl-cyclopent-1-enyl)-phenyl-methyl]-1H-indol-3-yl}-ethyl)-acetamide, N-(2-{2-[(2-Hydroxy-5-oxo-3-phenyl-cyclopent-1-enyl)-phenyl-methyl]-5-methyl-1H-indol-3-yl}-ethyl)-acetamide, 2-{[3-(2-Amino-ethyl)-6-ethyl-1H-indol-2-yl]-phenyl-methyl}-3-hydroxy-4-phenyl-cyclopent-2-enone or N-(2-{6-Chloro-2-[(2-hydroxy-5-oxo-3-phenyl-cyclopent-1-enyl)-phenyl-methyl]-1H-indol-3-yl}-1,1-dimethyl-ethyl)-acetamide.

The compounds of the present invention can be prepared, for example, by the general synthetic procedures described below.

General Synthetic Procedures

Abbreviations:

DMSO: Dimethylsulfoxid

LDA: Lithiumdiisopropyl amide

THF: Tetrahydrofurane

I) The compounds of formula (I) can be prepared in accordance with the following scheme 1:

Scheme 1

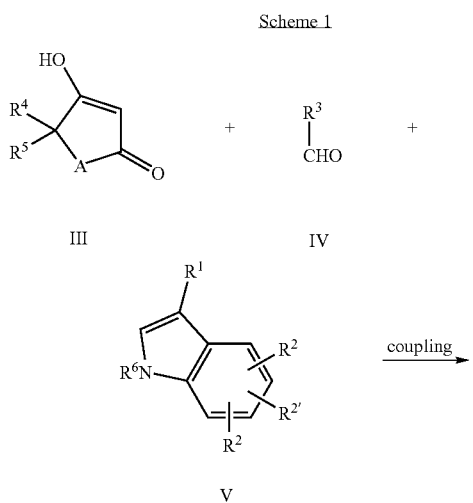

-continued

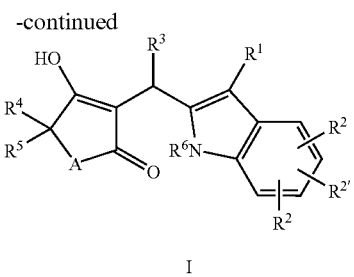

I

A, $R^1$, $R^2$, $R^{2'}$, $R^{2''}$, $R^3$, $R^4$, $R^5$ and $R^6$ are as defined before.

The coupling of an vinylogous acid III, an aldehyde IV and an indole V to the vinylogous acid I can be effected in a solvent such as $CH_3CN$ or an acid such as a carbonic acid, e.g. formic acid or preferably acetic acid at a temperature in the range of 20-100° C., preferably at 70° C. for 1-20 hours.

II)-i) The starting materials of formula III (A=O) may be prepared in accordance with the following scheme 2:

Scheme 2

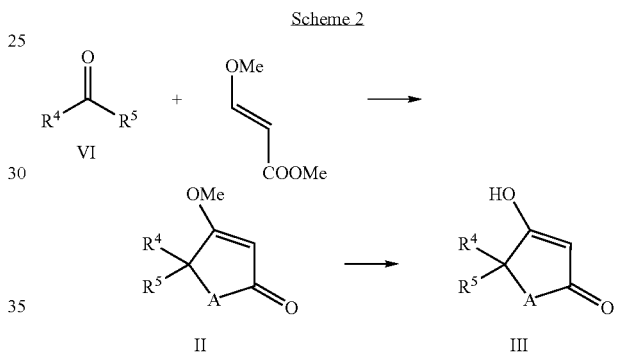

$R^4$ and $R^5$ are as defined before.

Aldehydes or ketones VI may be reacted with 3(E)-methoxy-acrylic acid methyl ester (Miyata, Okiko; Schmidt, Richard R.; Angewandte Chemie (1982), 94(8), 651-2) in solvents like diethyl ether or THF in the presence of a base like lithiumdiisopropylamide at a temperature in the range of −100° C. to −50° C., preferably at −80° C. to give the tetronic acid methylester II (A=O). Cleavage of the methoxy group in II (A=O) may be accomplished with a strong mineral acid such as HI, HBr or HCl preferably HBr in water and acetic acid at a temperature in the range of 20° C. to 100° C., preferably at 40° C. to give the tetronic acid III (A=O).

II)-ii) The starting materials of formula III (A=NH or A=N—$C_{1-6}$ alkyl) may be prepared in accordance with the following scheme 3 as described by Hofheinz, Werner et al., Helvetica Chimica Acta (1977), 60(2), 660-9 or Hilpert, Hans et al., U.S. Pat. Appl. Publ. (2005), US2005119329:

Scheme 3

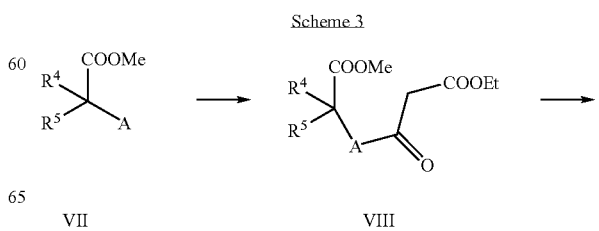

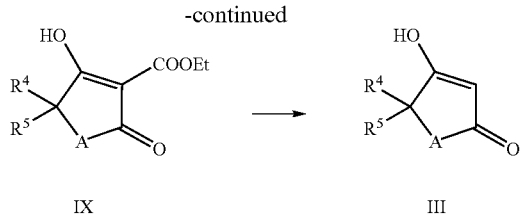

Aminoacid methylester VII may be reacted with chlorocarbonyl-acetic acid ethyl ester in solvents like diethyl ether, THF or preferably dichloromethane in the presence of a base like an alkylamine preferably triethylamine at a temperature in the range of 0° C. to 60° C., preferably at 22° C. to give the malonamide VIII (A=NH or A=N—$C_{1-6}$ alkyl).

Cyclization of the malonamide VIII may be effected with a strong base, e.g. sodium t-amylate, potassium t-butoxide or preferably potassium hexamethyldisilazide in a solvent like diethylether, THF, benzene or preferably toluene, at a temperature in the range of 0° C.-60° C., preferably at 22° C. to give the tetramic acid derivative IX (A=NH or A=N—$C_{1-6}$ alkyl).

Decarboxylation of the tetramic acid derivative IX may be accomplished in the presence of a weak and a strong acid such as acetic acid and trifluoroacetic acid at 22° C. to 100° C. preferably at 80° C. to give the tetramic acid III (A=NH or A=N—$C_{1-6}$ alkyl).

II)-iii) The starting materials of formula III (A=$CH_2$) can be prepared according to Nguyen, Hanh Nho et al., Journal of the American Chemical Society (2003), 125(39), 11818-11819 or Hamer, Neil K. et al., Tetrahedron Letters (1986), 27(19), 2167-8.

II)-iv) The starting materials of formula III can also be prepared according to the following literature references 11) Hofheinz, Werner et al., Helvetica Chimica Acta (1977), 60(2), 660-9;
12) Galeotti, Nathalie et al., Journal of Organic Chemistry (1993), 58(20), 5370-6;
13) Hilpert, Hans et al., U.S. Pat. Appl. Publ. (2005), US2005119329;
14) Krepski, Larry R. et al., Tetrahedron Letters (1985), 26(8), 981-4;
15) Compain, Philippe et al., Synlett (1994), (11), 943-5;
16) Nguyen, Hanh Nho et al., Journal of the American Chemical Society (2003), 125(39), 11818-11819;
17) Hamer, Neil K. et al., Tetrahedron Letters (1986), 27(19), 2167-8.
18) Matsuo, Keizo et al., Chemical & Pharmaceutical Bulletin (1984), 32(9), 3724-9.
19) Mizuno, Hatsuhiko et al., Chemical & Pharmaceutical Bulletin (1975), 23(3), 527-37.

III) The starting materials of formula IV are all commercially available.

IV) The starting materials of formula V are commercially available or they can be prepared according to the following literature references:

1) Ho, Beng T. et al., Journal of Medicinal Chemistry (1971), 4(6);
2) Hasegawa, Masakazu et al., Heterocycles (1999), 51(12), 2815-2821;
3) Contour-Galcera, Marie-Odile, et al., Bioorganic & Medicinal Chemistry Letters (2005), 5(15), 3555-3559;
4) Khalil, Ehab M. et al., Journal of Biological Chemistry (1998), 273(46), 30321-30327;
5) Nenajdenko, Valentine G. et al., Tetrahedron (2004), 60(51), 11719-11724;
6) Cheve, Gwenael et al., Medicinal Chemistry Research (2002), 11(7), 361-379;
7) Mor, Marco et al., Journal of Medicinal Chemistry (1998), 41(20), 3831-3844;
8) Heath-Brown, B. et al., Journal of the Chemical Society, Abstracts (1965), (December), 7165-78;
9) Bastian, Jolie Anne et al., W.O. Pat. Appl. Publ. (2003), WO2003016307;
10) D. Nagarathnam et al., Synthetic Communications (1993) 23 (14), 2011-2017.
20) Hengartner, Urs et al., Journal of Organic Chemistry (1979), 44(22), 3741-7.
21) Yang, Shyh-Chyun et al., Indian Journal of Chemistry, Section B: Organic Chemistry Including Medicinal Chemistry (1999), 38B(8), 897-904.
22) Tsuchiya, Michihiro et al., international patent application, WO8200032 (1982).
23) Pfister, Burg R. et al., U.S. pat. No. 5,436,264 (1995).

As described above, the compounds of formula (I) are active compounds and inhibit chymase. These compounds consequently prevent the activation of angiotensin II, endothelin, TGFb, Il1, SCF, collagenase and degradation of proteins like thrombin, FN, APO A1,2. They therefore can be used for the treatment and/or prevention of allergic, inflammatory and/or fibrotic diseases, such as allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel disease, Crohns' disease, atherothrombosis and/or burns/ulcers in Diabetes/CLI.

Prevention and/or treatment of allergic, inflammatory or fibrotic diseases, particularly atherothrombosis or asthma, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of allergic, inflammatory and/or fibrotic diseases, particularly as therapeutically active substances for the treatment and/or prophylaxis of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

The invention also relates to the use of compounds as described above for the preparation of medicaments for the therapeutic and/or prophylactic treatment of allergic, inflammatory and/or fibrotic diseases, particularly for the therapeutic and/or prophylactic treatment of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel disease, Crohns' disease, atherothrombosis and/or burns/ulcers in Diabetes/CLI. Such medicaments comprise a compound as described above.

The invention also relates to the process and the intermediates for manufacturing the compounds of formula (I) as well as the process for manufacturing the intermediates.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

General Procedure A: Preparation of the Tetronic Acid Methylesters II (A=O)

To a solution of 20 ml of LDA (2M in THF) and 130 ml of THF was added at −95° C. to −100° C. a solution of 5.47 g of 3(E)-methoxy-acrylic acid methyl ester in 4.5 ml of THF within 1 min, stirring was continued at the same temperature for 5 min, which was followed by the addition of a pre-cooled (−78° C.) solution of the aldehyde (33 mmole) in 4.5 ml of THF within 2 min and stirring was continued at −100° C. for 30 min and at −78° C. for 1 h. The cold solution was poured onto 130 ml of ice-water, the pH was adjusted to 4 with 6.5 ml of aqueous HCl (37%) and the layers were separated. The aqueous layer was extracted twice with dichloromethane, the organic layers were washed with brine, dried and evaporated. The residue was chromatographed on silica (n-heptane/AcOEt, various ratios) to give the tetronic acid methylesters II (A=O).

General Procedure B: Preparation of the Tetronic Acids III (A=O)

A mixture of the tetronic acid methylester II (A=O, 10 mmole) and 15 ml of aqueous HCl (37%) was stirred at 40° C. until completion of the reaction. The suspension was filtered and the residue washed with ice-cold water and dried. An oily reaction mixture was extracted with dichloromethane, the organic layers were washed with brine, dried and evaporated. The residue was either triturated with AcOEt/hexane or chromatographed with dichloromethane/MeOH (various ratios) to give the tetronic acids III (A=O).

General Procedure C: Preparation of the Tetramic Acids III (A=NH or A=N—$C_{1-6}$ alkyl)

To a mixture of the aminoacid methylester VII (A=$NH_2$ or A=N(H)($C_{1-6}$ alkyl), 18 mmole) in dichloromethane (60 ml) was subsequently added at 0° C. triethylamine (56 mmole) and chlorocarbonyl-acetic acid ethyl ester (21.5 mmole) and stirring was continued overnight. The suspension was filtered, the filtrate evaporated and the residue was partitioned between diluted aqueous hydrochloric acid and ethyl acetate. The organic layer was dried evaporated and the residue chromatographed on silica using cyclohexane/ethyl acetate (2:1) to give the malonamide VIII (A=NH or A=N—$C_{1-6}$ alkyl).

A mixture of the malonamide VIII (A=NH or A=N—$C_{1-6}$ alkyl, 7 mmole) in toluene (12 ml) was treated at 22° C. with a solution of potassium hexamethyldisilazide in THF (0.9 M, 7 mmole) and stirring was continued for 1-16 h. The suspension was filtered and the residue dried to give the tetramic acid derivative IX (A=NH or A=N—$C_{1-6}$ alkyl).

A mixture of the tetramic acid derivative IX (A=NH or A=N—$C_{1-6}$ alkyl, 7 mmole) in acetic acid (40 ml) and trifluoroacetic acid (4 ml) was heated to reflux for 1-5 h. The mixture was evaporated and the residue chromatographed on silica using diethyl ether to give the tetramic acid III (A=NH or A=N—$C_{1-6}$ alkyl).

EXAMPLE A

Preparation of 4-Hydroxy-5-methyl-5-phenyl-5H-furan-2-one

A1. Using general procedure A, acetophenone was reacted with 3(E)-methoxy-acrylic acid methyl ester to give rac-4-methoxy-5-methyl-5-phenyl-5H-furan-2-one as a colorless solid. MS: 204.1 ([M]$^+$).

A2. rac-4-Methoxy-5-methyl-5-phenyl-5H-furan-2-one (0.50 g) was separated on a Chiralpack AD using n-heptane/ethanol 9:1 to give (S)-4-methoxy-5-methyl-5-phenyl-5H- furan-2-one (0.24 g as the faster eluting peak and (R)-4-methoxy-5-methyl-5-phenyl-5H-furan-2-one (0.24 g) as the slower eluting peak.

A3. Using general procedure B, (S)-4-methoxy-5-methyl-5-phenyl-5H-furan-2-one was hydrolyzed to give (S)-4-hydroxy-5-methyl-5-phenyl-5H-furan-2-one as a colorless solid. MS: 190.2 ([M]$^+$). [α]$_{365nm}$: −420.4° (1%, CHCl$_3$).

A4. Using general procedure B, (R)-4-methoxy-5-methyl-5-phenyl-5H-furan-2-one was hydrolyzed to give (R)-4-hydroxy-5-methyl-5-phenyl-5H-furan-2-one as a colorless solid. MS: 190.2 ([M]$^+$). [α]$_{365nm}$: +441.5° (1%, CHCl$_3$).

EXAMPLE B

Preparation of rac-5-(2-Cyclohexyl-ethyl)-4-hydroxy-5H-furan-2-one

B1. Using general procedure A, cyclohexanepropanal (Stratakis, Manolis et al., Journal of Organic Chemistry (2002), 67(25), 8758-8763) was reacted with 3(E)-methoxyacrylic acid methyl ester to give rac-5-(2-cyclohexyl-ethyl)-4-methoxy-5H-furan-2-one as a colorless solid. MS: 225.2 ([M+H]$^+$).

B2. Using general procedure B, rac-5-(2-cyclohexyl-ethyl)-4-methoxy-5H-furan-2-one was hydrolyzed to give rac-5-(2-cyclohexyl-ethyl)-4-hydroxy-5H-furan-2-one as a brown solid. MS: 211.1 ([M+H]$^+$).

EXAMPLE C

Preparation of rac-1-hydroxy-7a-methyl-5,6,7,7a-tetrahydro-pyrrolizin-3-one

Using general procedure C, rac-2-methyl-pyrrolidine-2-carboxylic acid methylester was converted to the title compound obtained as a yellow solid. MS: 154.3 ([M+H]$^+$).

EXAMPLE D

Preparation of (R)-5-benzyl-4-hydroxy-5-methyl-1,5-dihydro-pyrrol-2-one

Using general procedure C, (R)-2-amino-2-methyl-3-phenyl-propionic acid methylester was converted to the title compound obtained as a white solid. MS: 204.1 ([M+H]$^+$).

EXAMPLE E

Preparation of (R)-4-hydroxy-5-isopropyl-5-methyl-1,5-dihydro-pyrrol-2-one

Using general procedure C, (R)-2-amino-2,3-dimethyl-butyric acid methyl ester was converted to the title compound obtained as a white solid. MS: 156.3 ([M+H]$^+$).

EXAMPLE F

Preparation of (R)-4-hydroxy-5-methyl-5-phenyl-1,5-dihydro-pyrrol-2-one

Using general procedure C, (R)-2-amino-2-phenyl-propionic acid methyl ester was converted to the title compound [Lit. 19] obtained as a colorless oil. MS: 190.3 ([M+H]$^+$). [α]$_{365nm}$: +360.9° (c=1%, CHCl$_3$).

General Procedure D: Coupling of an Vinylogous Acid III an Aldehyde IV and an Indole V A solution of the vinylogous acid (1 mmole), the aldehyde (1.3 mmole) and the indole (1 mmole) in actic acid (2 ml) was stirred at 70° C. for 16 h. The suspension was filtered and the residue washed with MeOH/Et$_2$O (1:10). If no precipitations occurred, the solution was purified on preparative HPLC (RP-18, CH$_3$CN/H$_2$O, gradient).

EXAMPLE 1

N-(2-{2-[(4-Hydroxy-5-isopropyl-2-oxo-2,5-dihydro-1H-pyrrol-3-yl)-phenyl-methyl]-1H-indol-3-yl}-ethyl)-acetamide

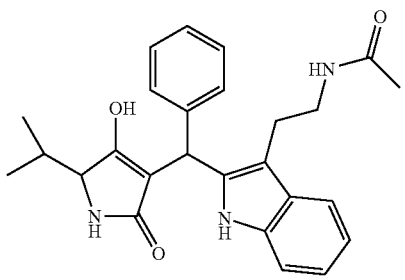

Using general procedure C, 4-hydroxy-5-isopropyl-1,5-dihydro-pyrrol-2-one (Literature (hereinafter mentioned as Lit.). 11) was reacted with benzaldehyde and N-[2-(1H-indol-3-yl)-ethyl]-acetamide to give the title compound as a pale yellow solid. MS: 432.5 ([M+H]$^+$).

EXAMPLE 2

N-(2-{2-[(3-Fluoro-phenyl)-(4-hydroxy-5-isopropyl-2-oxo-2,5-dihydro-1H-pyrrol-3-yl)-methyl]-1H-indol-3-yl}-ethyl)-acetamide

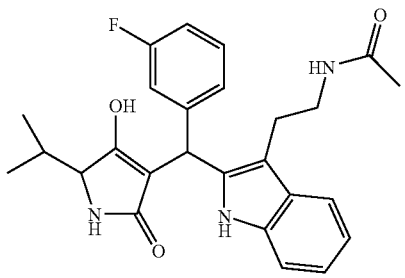

Using general procedure C, 4-hydroxy-5-isopropyl-1,5-dihydro-pyrrol-2-one (Lit. 11) was reacted with 3-fluoro-benzaldehyde and N-[2-(1H-indol-3-yl)-ethyl]-acetamide to give the title compound as a yellow solid. MS: 450.1 ([M+H]$^+$).

EXAMPLE 3

N-(2-{2-[(4-Fluoro-phenyl)-(4-hydroxy-5-isopropyl-2-oxo-2,5-dihydro-1H-pyrrol-3-yl)-methyl]-1H-indol-3-yl}-ethyl)-acetamide

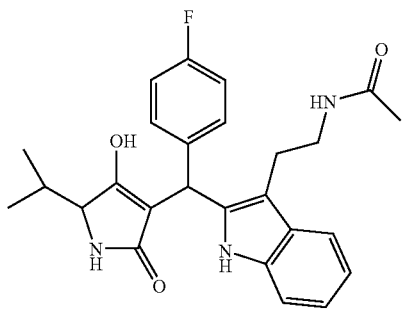

Using general procedure C, 4-hydroxy-5-isopropyl-1,5-dihydro-pyrrol-2-one (Lit. 11) was reacted with 4-fluoro-benzaldehyde and N-[2-(1H-indol-3-yl)-ethyl]-acetamide to give the title compound as a yellow solid. MS: 450.3 ([M+H]$^+$).

EXAMPLE 4

N-(2-{2-[(3,5-Difluoro-phenyl)-(4-hydroxy-5-isopropyl-2-oxo-2,5-dihydro-1H-pyrrol-3-yl)-methyl]-1H-indol-3-yl}-ethyl)-acetamide

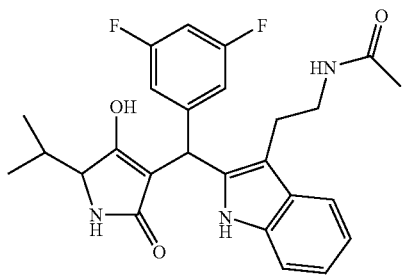

Using general procedure C, 4-hydroxy-5-isopropyl-1,5-dihydro-pyrrol-2-one (Lit. 11) was reacted with 3,5-difluoro-benzaldehyde and N-[2-(1H-indol-3-yl)-ethyl]-acetamide to give the title compound as a yellow solid. MS: 468.0 ([M+H]$^+$).

EXAMPLE 5

Acetic acid 2-{2-[(4-hydroxy-5-isopropyl-2-oxo-2,5-dihydro-1H-pyrrol-3-yl)-phenyl-methyl]-1H-indol-3-yl}-ethyl ester

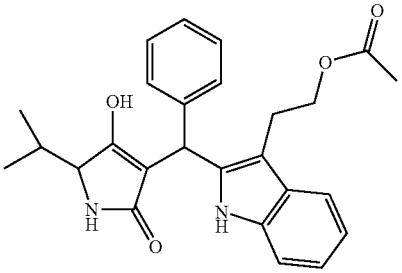

Using general procedure C, 4-hydroxy-5-isopropyl-1,5-dihydro-pyrrol-2-one (Lit. 11) was reacted with benzaldehyde and 2-(1H-indol-3-yl)-ethanol to give the title compound as an orange foam. MS: 433.3 ([M+H]$^+$).

EXAMPLE 6

4-Hydroxy-3-{[3-(2-hydroxy-ethyl)-1H-indol-2-yl]-phenyl-methyl}-5-isopropyl-1,5-dihydro-pyrrol-2-one

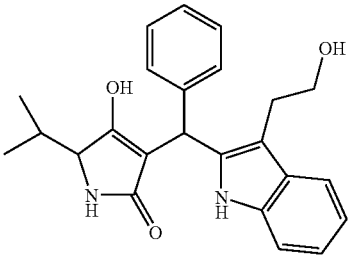

A solution of acetic acid 2-{2-[(4-hydroxy-5-isopropyl-2-oxo-2,5-dihydro-1H-pyrrol-3-yl)-phenyl-methyl]-1H-indol-3-yl}-ethyl ester (40 mg) and LiOH (8.5 mg) in MeOH (0.5 ml) was stirred at 22° C. for 30 min and evaporated. The residue was partitioned between 0.1 N aqueous HCl and AcOEt and the organic layer was dried and evaporated. The residue was chromatographed on silica using CH$_2$Cl$_2$/MeOH (10:3) to give the title compound as an orange foam. MS: 391.1 ([M+H]$^+$).

EXAMPLE 7

N-(2-{2-[(4-Hydroxy-5-isopropyl-2-oxo-2,5-dihydro-1H-pyrrol-3-yl)-phenyl-methyl]-1H-indol-3-yl}-ethyl)-benzamide

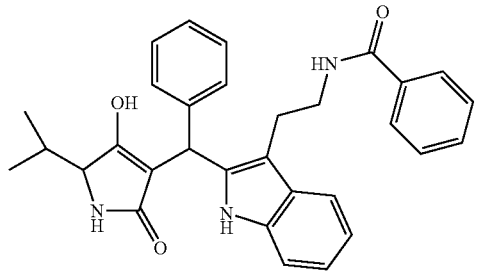

Using general procedure C, 4-hydroxy-5-isopropyl-1,5-dihydro-pyrrol-2-one (Lit. 11) was reacted with benzaldehyde and N-[2-(1H-indol-3-yl)-ethyl]-benzamide to give the title compound as a grey solid. MS: 494.3 ([M+H]$^+$).

EXAMPLE 8

N-(2-{2-[(4-Hydroxy-5-isopropyl-2-oxo-2,5-dihydro-1H-pyrrol-3-yl)-phenyl-methyl]-1H-indol-3-yl}-ethyl)-3,5-bis-trifluoromethyl-benzamide

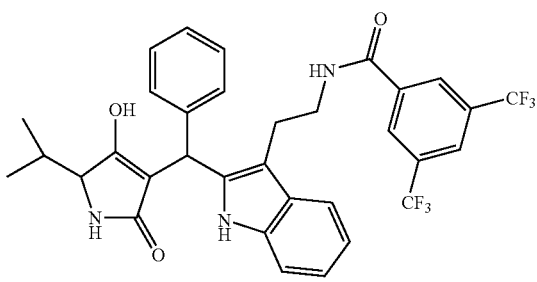

8.1. Preparation of N-[2-(1H-Indol-3-yl)-ethyl]-3,5-bis-trifluoromethyl-benzamide To a solution of 2-(1H-indol-3-yl)-ethylamine (1.0 g) in CH$_2$Cl$_2$ was added at 22° C. NEt$_3$ (1.74 ml) and 3,5-bis-trifluoromethyl-benzoyl chloride (1.24 ml) and stirring was continued at 22° C. for 16 h. The mixture was washed with aqueous NaHCO$_3$ and brine and the organic layer was dried and evaporated to give the title compound as a brown solid. MS: 401.3 ([M+H]$^+$).

8.2. Using general procedure C, 4-hydroxy-5-isopropyl-1,5-dihydro-pyrrol-2-one (Lit. 11) was reacted with benzaldehyde and N-[2-(1H-Indol-3-yl)-ethyl]-3,5-bis-trifluoromethyl-benzamide to give N-(2-{2-[(4-hydroxy-5-isopropyl-2-oxo-2,5-dihydro-1H-pyrrol-3-yl)-phenyl-methyl]-1H-indol-3-yl}-ethyl)-3,5-bis-trifluoromethyl-benzamide as a red solid. MS: 630.2 ([M+H]$^+$).

EXAMPLE 9

Naphthalene-2-sulfonic acid (2-{2-[(4-hydroxy-5-isopropyl-2-oxo-2,5-dihydro-1H-pyrrol-3-yl)-phenyl-methyl]-1H-indol-3-yl}-ethyl)-amide

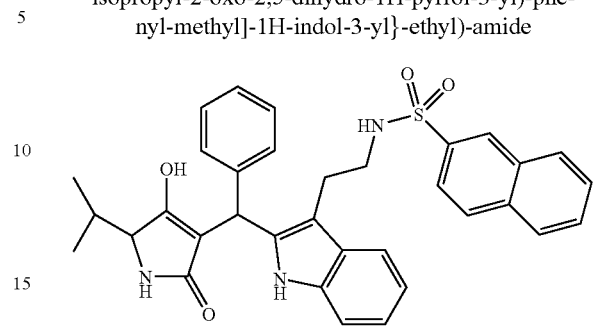

Using general procedure C, 4-hydroxy-5-isopropyl-1,5-dihydro-pyrrol-2-one (Lit. 11) was reacted with benzaldehyde and naphthalene-2-sulfonic acid [2-(1H-indol-3-yl)-ethyl]-amide (Lit. 1) to give the title compound as an orange solid. MS: 580.3 ([M+H]$^+$).

EXAMPLE 10

3-[(5-Fluoro-3-methyl-1H-indol-2-yl)-phenyl-methyl]-4-hydroxy-5-isopropyl-1,5-dihydro-pyrrol-2-one

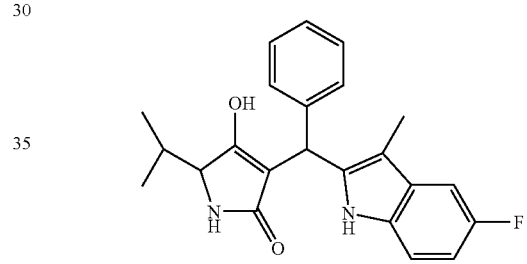

Using general procedure C, 4-hydroxy-5-isopropyl-1,5-dihydro-pyrrol-2-one (Lit. 11) was reacted with benzaldehyde and 5-fluoro-3-methyl-1H-indole to give the title compound as a yellow solid. MS: 377.1 ([M−H]$^-$).

EXAMPLE 11

3-[(5-Fluoro-3-methyl-1H-indol-2-yl)-phenyl-methyl]-4-hydroxy-5-isopropyl-1-methyl-1,5-dihydro-pyrrol-2-one

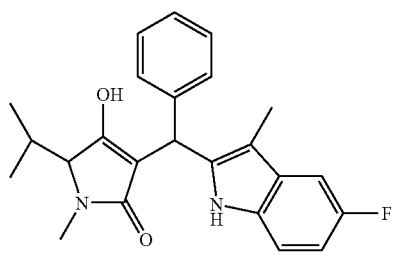

Using general procedure C, 4-hydroxy-5-isopropyl-1-methyl-1,5-dihydro-pyrrol-2-one (Lit. 12) was reacted with benzaldehyde and 5-fluoro-3-methyl-1H-indole to give the title compound as a yellow solid. MS: 391.3 ([M−H]−).

EXAMPLE 12

4-Hydroxy-5-isopropyl-3-[(3-methyl-1H-indol-2-yl)-phenyl-methyl]-1,5-dihydro-pyrrol-2-one

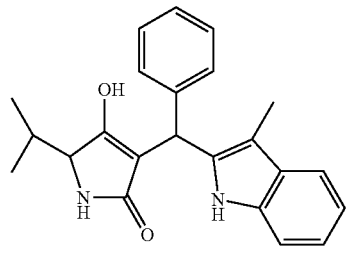

Using general procedure C, 4-hydroxy-5-isopropyl-1,5-dihydro-pyrrol-2-one (Lit. 11) was reacted with benzaldehyde and 3-methyl-1H-indole to give the title compound as a yellow solid. MS: 361.0 ([M+H]+).

EXAMPLE 13

3-[(5-Fluoro-3-isopropyl-1H-indol-2-yl)-phenyl-methyl]-4-hydroxy-5-isopropyl-1,5-dihydro-pyrrol-2-one

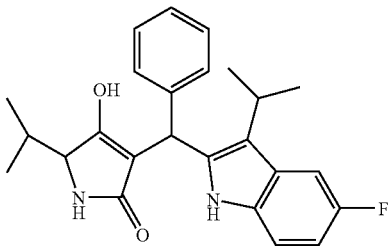

13.1. 5-fluoro-3-isopropyl-1H-indole was prepared in analogy to Lit. 10 as a brownish oil, MS: 177.0 ([M]+).

13.2. Using general procedure C, 4-hydroxy-5-isopropyl-1,5-dihydro-pyrrol-2-one (Lit. 11) was reacted with benzaldehyde and 5-fluoro-3-isopropyl-1H-indole to give 3-[(5-fluoro-3-isopropyl-1H-indol-2-yl)-phenyl-methyl]-4-hydroxy-5-isopropyl-1,5-dihydro-pyrrol-2-one as a orange solid. MS: 405.2 ([M−H]−).

EXAMPLE 14

N-(2-{2-[(4-Hydroxy-2-oxo-2,5-dihydro-furan-3-yl)-phenyl-methyl]-1H-indol-3-yl}-ethyl)-acetamide

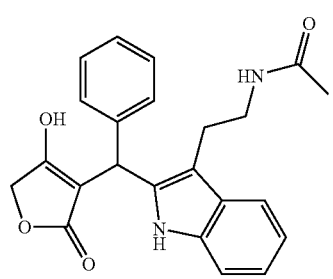

Using general procedure C, 4-hydroxy-5H-furan-2-one was reacted with benzaldehyde and N-[2-(1H-indol-3-yl)-ethyl]-acetamide to give the title compound as orange foam. MS: 391.1 ([M+H]+).

EXAMPLE 15

N-(2-{2-[(5-Benzyl-4-hydroxy-2-oxo-2,5-dihydro-furan-3-yl)-phenyl-methyl]-1H-indol-3-yl}-ethyl)-acetamide

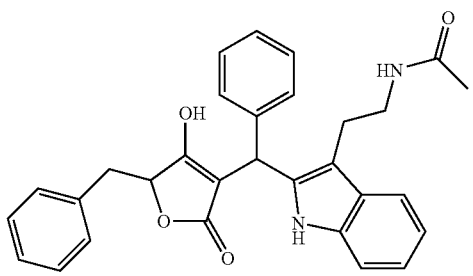

Using general procedure C, 5-benzyl-4-hydroxy-5H-furan-2-one (Lit. 13) was reacted with benzaldehyde and N-[2-(1H-indol-3-yl)-ethyl]-acetamide to give the title compound as a white solid. MS: 481.0 ([M+H]+).

EXAMPLE 16

N-(2-{2-[(5-Benzyl-4-hydroxy-2-oxo-2,5-dihydro-furan-3-yl)-phenyl-methyl]-6-fluoro-1H-indol-3-yl}-ethyl)-acetamide

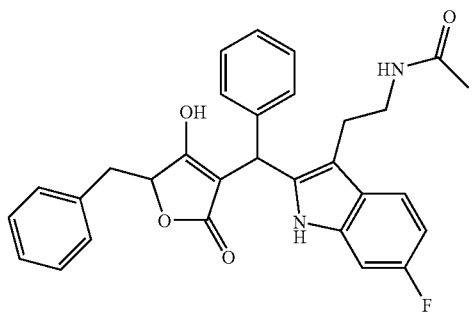

16.1. N-[2-(6-Fluoro-1H-indol-3-yl)-ethyl]-acetamide

To a solution of 2-(6-fluoro-1H-indol-3-yl)-ethylamine (0.88 g) and NEt3 (2.27 ml) in CH$_2$Cl$_2$ (8 ml) was added acetic acid anhydride (0.43 ml) and stirring was continued at 22° C. for 1 h. The mixture was washed with 1 N aqueous HCl, the organic layer was dried and evaporated. The residue was chromatographed on silica using CH$_2$Cl$_2$/MeOH (25:1) to give the title compound as a pale yellow oil. MS: 219.1 ([M−H]$^-$).

16.2. Using general procedure C, 5-benzyl-4-hydroxy-5H-furan-2-one (Lit. 13) was reacted with benzaldehyde and N-[2-(6-fluoro-1H-indol-3-yl)-ethyl]-acetamide to give N-(2-{2-[(5-benzyl-4-hydroxy-2-oxo-2,5-dihydro-furan-3-yl)-phenyl-methyl]-6-fluoro-1H-indol-3-yl}-ethyl)-acetamide as a white solid. MS: 497.4 ([M−H]$^-$).

EXAMPLE 17

N-(2-{2-[(5-Benzyl-4-hydroxy-2-oxo-2,5-dihydro-furan-3-yl)-phenyl-methyl]-5-chloro-1H-indol-3-yl}-ethyl)-acetamide

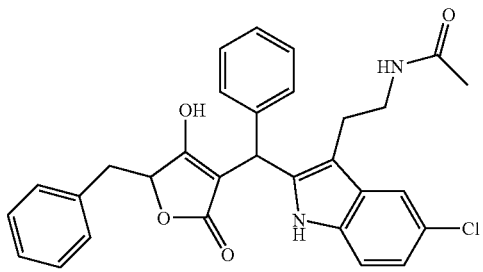

Using general procedure C, 5-benzyl-4-hydroxy-5H-furan-2-one (Lit. 13) was reacted with benzaldehyde and N-[2-(5-chloro-1H-indol-3-yl)-ethyl]-acetamide (Lit. 2) to give the title compound as a white solid. MS: 513.1 ([M−H]$^-$).

EXAMPLE 18 AND 19

5-Benzyl-3-{[6-fluoro-3-(2-hydroxy-ethyl)-1H-indol-2-yl]-phenyl-methyl}-4-hydroxy-5H-furan-2-one and Acetic acid 2-{2-[(5-benzyl-4-hydroxy-2-oxo-2,5-dihydro-furan-3-yl)-phenyl-methyl]-6-fluoro-1H-indol-3-yl}-ethyl ester

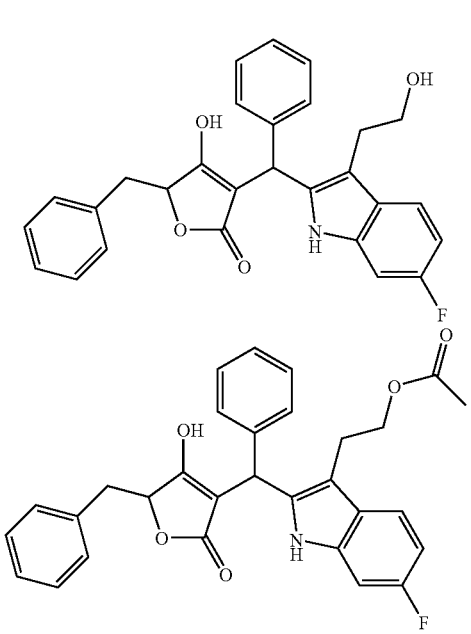

Using general procedure C, 5-benzyl-4-hydroxy-5H-furan-2-one (Lit. 13) was reacted with benzaldehyde and 2-(6-fluoro-1H-indol-3-yl)-ethanol (Lit. 3). The mixture was separated by HPLC to give the first title compound as a pale brown solid. MS: 456.3 ([M−H]$^-$). The second fraction contained the second title compound as an orange. MS: 498.1 ([M−H]$^-$).

EXAMPLE 20

N-(2-{2-[1-(5-Benzyl-4-hydroxy-2-oxo-2,5-dihydro-furan-3-yl)-2-methyl-propyl]-1H-indol-3-yl}-ethyl)-acetamide

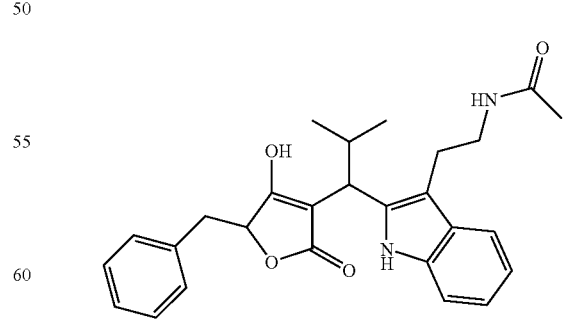

Using general procedure C, 5-benzyl-4-hydroxy-5H-furan-2-one (Lit. 13) was reacted with 2-methyl-propionaldehyde and N-[2-(1H-indol-3-yl)-ethyl]-acetamide) to give the title compound as a yellow solid. MS: 445.1 ([M−H]$^-$).

EXAMPLE 21

N-(2-{2-[1-(5-Benzyl-4-hydroxy-2-oxo-2,5-dihydro-furan-3-yl)-3-methyl-butyl]-1H-indol-3-yl}-ethyl)-acetamide

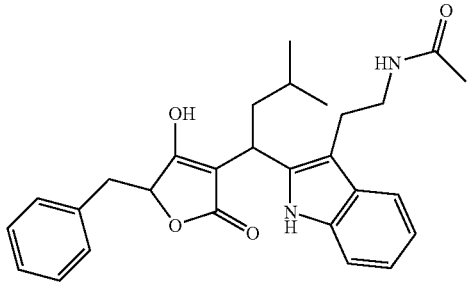

Using general procedure C, 5-benzyl-4-hydroxy-5H-furan-2-one (Lit. 13) was reacted with 3-methyl-butyraldehydeand and N-[2-(1H-indol-3-yl)-ethyl]-acetamide) to give the title compound as a yellow solid. MS: 459.1 ([M−H]$^-$).

EXAMPLE 22

N-(2-{2-[1-(5-Benzyl-4-hydroxy-2-oxo-2,5-dihydro-furan-3-yl)-pentyl]-1H-indol-3-yl}-ethyl)-acetamide

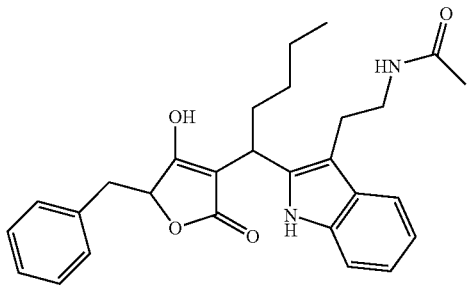

Using general procedure C, 5-benzyl-4-hydroxy-5H-furan-2-one (Lit. 13) was reacted with pentanal and N-[2-(1H-indol-3-yl)-ethyl]-acetamide) to give the title compound as a white solid. MS: 459.3 ([M−H]$^-$).

EXAMPLE 23

N-(2-{2-[1-(5-Benzyl-4-hydroxy-2-oxo-2,5-dihydro-furan-3-yl)-2-phenyl-ethyl]-1H-indol-3-yl}-ethyl)-acetamide

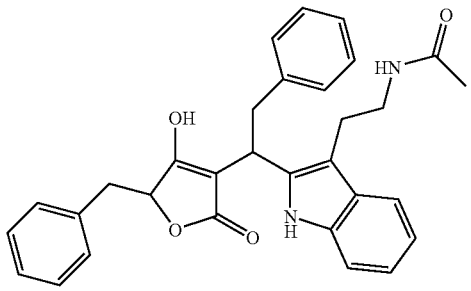

Using general procedure C, 5-benzyl-4-hydroxy-5H-furan-2-one (Lit. 13) was reacted with phenyl-acetaldehyde and N-[2-(1H-indol-3-yl)-ethyl]-acetamide) to give the title compound as a white solid. MS: 493.0 ([M−H]$^-$).

EXAMPLE 24

N-(2-{2-[1-(5-Benzyl-4-hydroxy-2-oxo-2,5-dihydro-furan-3-yl)-3-phenyl-propyl]-1H-indol-3-yl}-ethyl)-acetamide

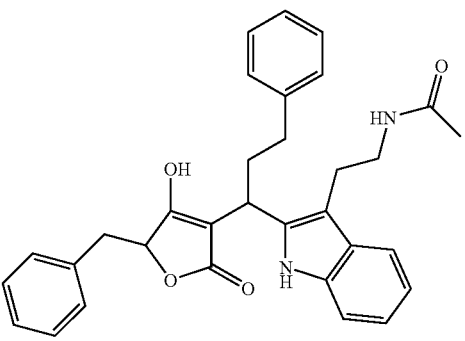

Using general procedure C, 5-benzyl-4-hydroxy-5H-furan-2-one (Lit. 13) was reacted with 3-phenyl-propionaldehyde and N-[2-(1H-indol-3-yl)-ethyl]-acetamide) to give the title compound as a yellow solid. MS: 507.2 ([M−H]$^-$).

EXAMPLE 25

N-(2-{2-[(5-Benzyl-4-hydroxy-2-oxo-2,5-dihydro-furan-3-yl)-(2-fluoro-phenyl)-methyl]-1H-indol-3-yl}-ethyl)-acetamide

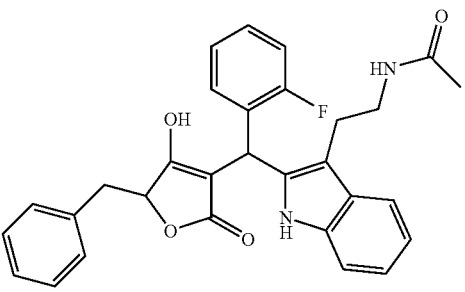

Using general procedure C, 5-benzyl-4-hydroxy-5H-furan-2-one (Lit. 13) was reacted with 2-fluoro-benzaldehyde and N-[2-(1H-indol-3-yl)-ethyl]-acetamide) to give the title compound as a white solid. MS: 497.3 ([M−H]$^-$).

EXAMPLE 26

3-{[3-(2-Amino-ethyl)-6-fluoro-1H-indol-2-yl]-phenyl-methyl}-5-benzyl-4-hydroxy-5H-furan-2-one; salt with acetic acid

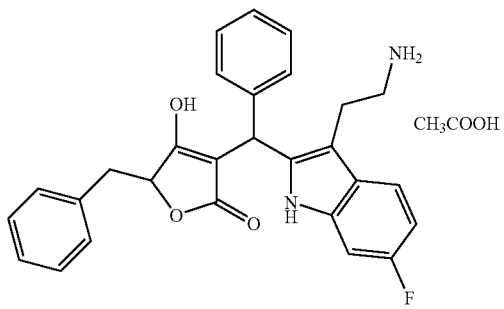

Using general procedure C, 5-benzyl-4-hydroxy-5H-furan-2-one (Lit. 13) was reacted with benzaldehyde and 2-(6-fluoro-1H-indol-3-yl)-ethylamine to give the title compound as pale red foam. MS: 457.1 ([M+H]+).

EXAMPLE 27

N-(2-{2-[(5-Benzyl-4-hydroxy-2-oxo-2,5-dihydro-furan-3-yl)-phenyl-methyl]-1H-indol-3-yl}-ethyl)-N-methyl-acetamide

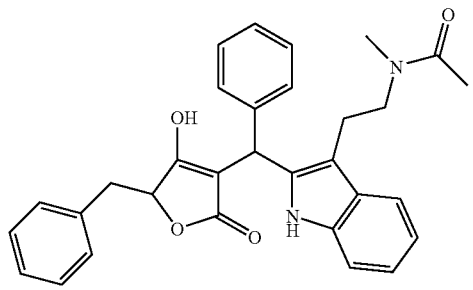

Using general procedure C, 5-benzyl-4-hydroxy-5H-furan-2-one (Lit. 13) was reacted with benzaldehyde and N-[2-(1H-indol-3-yl)-ethyl]-N-methyl-acetamide (Lit. 4) to give the title compound as pale yellow solid. MS: 493.3 ([M−H]−).

EXAMPLE 28

N-(2-{2-[(5-Benzyl-4-hydroxy-2-oxo-2,5-dihydro-furan-3-yl)-phenyl-methyl]-5-fluoro-1H-indol-3-yl}-ethyl)-acetamide

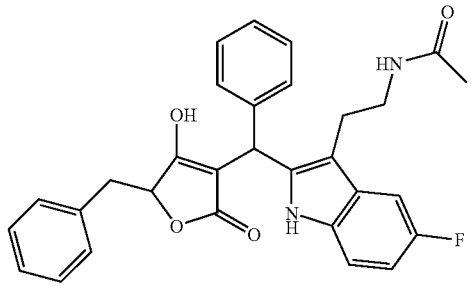

Using general procedure C, 5-benzyl-4-hydroxy-5H-furan-2-one (Lit. 13) was reacted with benzaldehyde and N-[2-(5-fluoro-1H-indol-3-yl)-ethyl]-acetamide (Lit. 5) to give the title compound as pale yellow solid. MS: 497.4 ([M−H]−).

EXAMPLE 29

N-(2-{2-[(5-Benzyl-4-hydroxy-2-oxo-2,5-dihydro-furan-3-yl)-phenyl-methyl]-1-methyl-1H-indol-3-yl}-ethyl)-acetamide

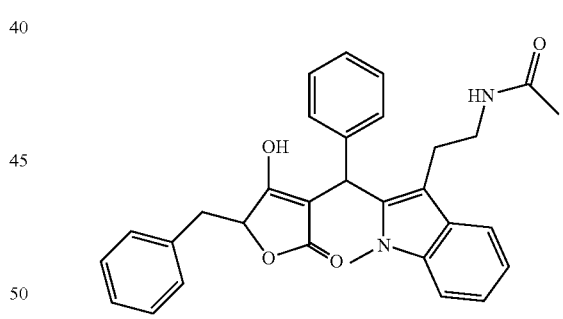

29.1. N-[2-(1-Methyl-1H-indol-3-yl)-ethyl]-acetamide was prepared from 2-(1-methyl-1H-indol-3-yl)-ethylamine by acylation as described in Example 16.1. to give a pale green oil, MS: 217.4 ([M+H]+).

Using general procedure C, 5-benzyl-4-hydroxy-5H-furan-2-one (Lit. 13) was reacted with benzaldehyde and N-[2-(1-methyl-1H-indol-3-yl)-ethyl]-acetamide to give N-(2-{2-[(5-benzyl-4-hydroxy-2-oxo-2,5-dihydro-furan-3-yl)-phenyl-methyl]-1-methyl-1H-indol-3-yl}-ethyl)-acetamide as red solid. MS: 493.3 ([M−H]−).

EXAMPLE 30

5-Benzyl-3-[(5-fluoro-3-methyl-1H-indol-2-yl)-phenyl-methyl]-4-hydroxy-5H-furan-2-one

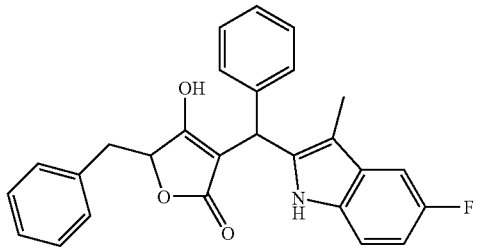

Using general procedure C, 5-benzyl-4-hydroxy-5H-furan-2-one (Lit. 13) was reacted with benzaldehyde and 5-fluoro-3-methyl-1H-indole to give the title compound as colorless solid. MS: 426.1 ([M−H]−).

EXAMPLE 31

N-(2-{6-Fluoro-2-[(4-hydroxy-2-oxo-5-phenyl-2,5-dihydro-furan-3-yl)-phenyl-methyl]-1H-indol-3-yl}-ethyl)-acetamide

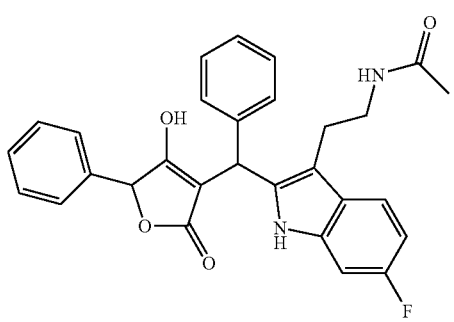

Using general procedure C, 4-hydroxy-5-phenyl-5H-furan-2-one (Lit. 14) was reacted with benzaldehyde and N-[2-(6-fluoro-1H-indol-3-yl)-ethyl]-acetamide (Example 18.1.) to give the title compound as pale brown solid. MS: 485.0 ([M+H]+).

EXAMPLE 32

3-{[3-(2-Amino-ethyl)-6-ethyl-1H-indol-2-yl]-phenyl-methyl}-4-hydroxy-5-phenyl-5H-furan-2-one

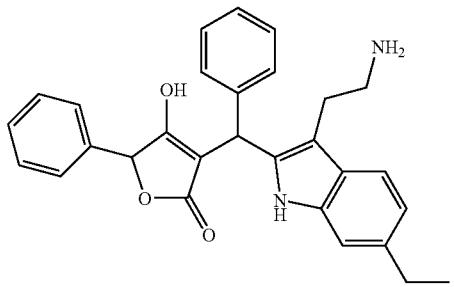

Using general procedure C, 4-hydroxy-5-phenyl-5H-furan-2-one (Lit. 14) was reacted with benzaldehyde and 2-(6-ethyl-1H-indol-3-yl)-ethylamine (Lit. 8) to give the title compound as a white solid; MS: 453.3 ([M+H]+).

EXAMPLE 33

N-(2-{6-Fluoro-2-[(4-hydroxy-5-methyl-2-oxo-5-phenyl-2,5-dihydro-furan-3-yl)-phenyl-methyl]-1H-indol-3-yl}-ethyl)-acetamide

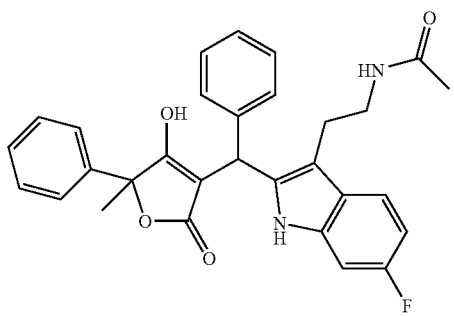

Using general procedure C, 4-hydroxy-5-methyl-5-phenyl-5H-furan-2-one (Example A2) was reacted with benzaldehyde and N-[2-(6-fluoro-1H-indol-3-yl)-ethyl]-acetamide (Example 18.1.) to give the title compound as pale brown solid. MS: 499.5 ([M+H]+).

EXAMPLE 34

N-(2-{2-[(4-Hydroxy-5-isobutyl-2-oxo-2,5-dihydro-furan-3-yl)-phenyl-methyl]-1H-indol-3-yl}-ethyl)-acetamide

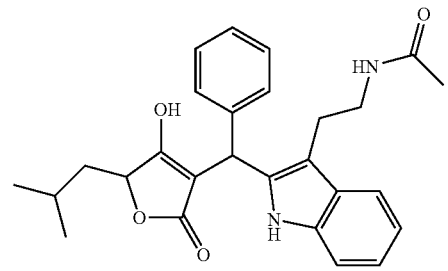

Using general procedure C, 4-hydroxy-5-isobutyl-5H-furan-2-one (Lit. 14) was reacted with benzaldehyde and N-[2-(1H-indol-3-yl)-ethyl]-acetamide to give the title compound as a white solid. MS: 441.1 ([M+H]+).

EXAMPLE 35

Acetic acid 2-{2-[(4-hydroxy-5-isobutyl-2-oxo-2,5-dihydro-furan-3-yl)-phenyl-methyl]-1H-indol-3-yl}-ethyl ester

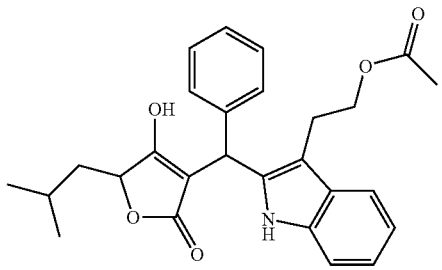

Using general procedure C, 4-hydroxy-5-isobutyl-5H-furan-2-one (Lit. 14) was reacted with benzaldehyde and 2-(1H-indol-3-yl)-ethanol to give the title compound as orange solid. MS: 448.1 ([M+H]$^+$).

EXAMPLE 36

N-(2-{2-[(4-Hydroxy-2-oxo-1-oxa-spiro[4.5]dec-3-en-3-yl)-phenyl-methyl]-1H-indol-3-yl}-ethyl)-acetamide

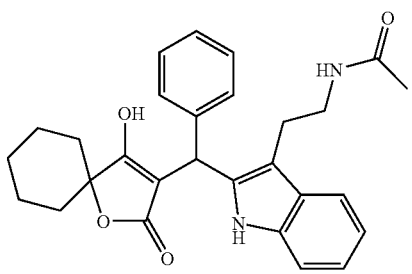

Using general procedure C, 4-hydroxy-1-oxa-spiro[4.5]dec-3-en-2-one (Lit. 15) was reacted with benzaldehyde and N-[2-(1H-indol-3-yl)-ethyl]-acetamide to give the title compound as a white solid. MS: 459.1 ([M+H]$^+$).

EXAMPLE 37

N-(2-{2-[(5-Cyclohexylmethyl-4-hydroxy-2-oxo-2,5-dihydro-furan-3-yl)-phenyl-methyl]-6-fluoro-1H-indol-3-yl}-ethyl)-acetamide

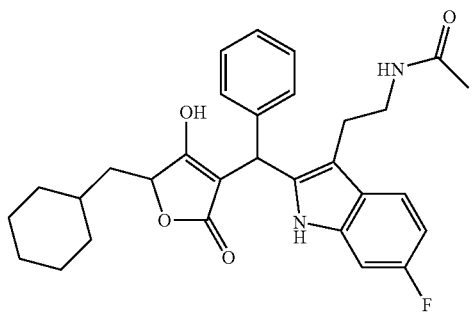

Using general procedure C, 5-cyclohexylmethyl-4-hydroxy-5H-furan-2-one (Lit. 13) was reacted with benzaldehyde and N-[2-(6-fluoro-1H-indol-3-yl)-ethyl]-acetamide (Example 18.1.) to give the title compound as pale red solid. MS: 503.0 ([M−H]$^-$).

EXAMPLE 38

N-[2-(2-{[5-(2-Cyclohexyl-ethyl)-4-hydroxy-2-oxo-2,5-dihydro-furan-3-yl]-phenyl-methyl}-6-fluoro-1H-indol-3-yl)-ethyl]-acetamide

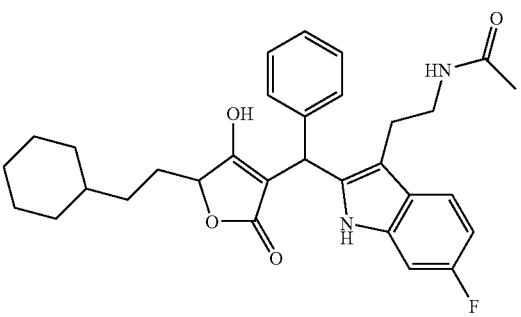

Using general procedure C, 5-(2-cyclohexyl-ethyl)-4-hydroxy-5H-furan-2-one (Example B2) was reacted with benzaldehyde and N-[2-(6-fluoro-1H-indol-3-yl)-ethyl]-acetamide (Example 18.1.) to give the title compound as pale green solid. MS: 517.2 ([M−H]$^-$).

EXAMPLE 39

N-(2-{6-Fluoro-2-[(4-hydroxy-2-oxo-5-phenethyl-2,5-dihydro-furan-3-yl)-phenyl-methyl]-1H-indol-3-yl}-ethyl)-acetamide

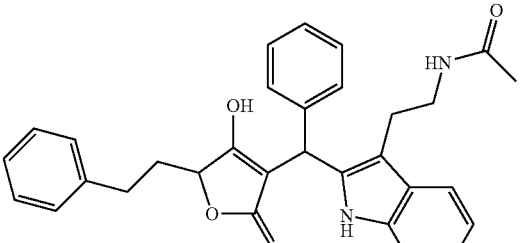

Using general procedure C, 4-hydroxy-5-phenethyl-5H-furan-2-one (Lit. 13) was reacted with benzaldehyde and N-[2-(6-fluoro-1H-indol-3-yl)-ethyl]-acetamide (Example 18.1.) to give the title compound as pale red solid. MS: 511.1 ([M−H]$^-$).

EXAMPLE 40

N-[2-(6-Fluoro-2-{[4-hydroxy-2-oxo-5-(3-phenyl-propyl)-2,5-dihydro-furan-3-yl]-phenyl-methyl}-1H-indol-3-yl)-ethyl]-acetamide

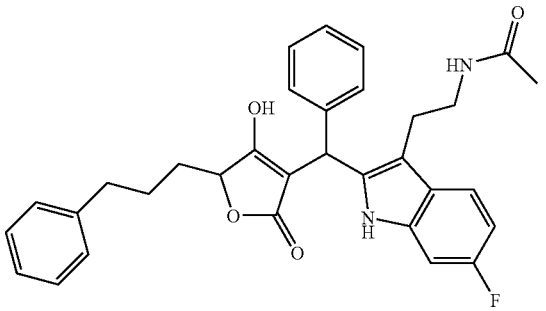

Using general procedure C, 4-hydroxy-5-(3-phenyl-propyl)-5H-furan-2-one (Lit. 13) was reacted with benzaldehyde and N-[2-(6-fluoro-1H-indol-3-yl)-ethyl]-acetamide (Example 18.1.) to give the title compound as pale red solid. MS: 525.2 ([M–H]$^-$).

EXAMPLE 41

N-(2-{2-[(2-Hydroxy-5-oxo-cyclopent-1-enyl)-phenyl-methyl]-1H-indol-3-yl}-ethyl)-acetamide

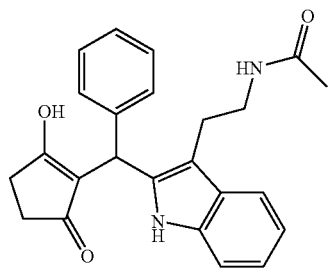

Using general procedure C, 3-hydroxy-cyclopent-2-enone (Lit. 16) was reacted with benzaldehyde and N-[2-(1H-indol-3-yl)-ethyl]-acetamide to give the title compound as a pink solid. MS: 387.4 ([M–H]$^-$).

EXAMPLE 42

N-(2-{2-[(2-Hydroxy-5-oxo-3-phenyl-cyclopent-1-enyl)-phenyl-methyl]-1H-indol-3-yl}-ethyl)-acetamide

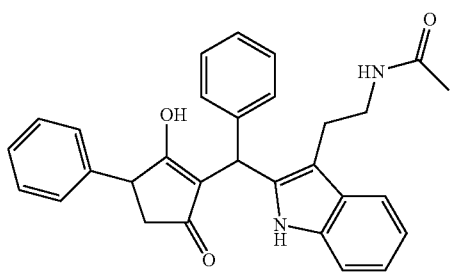

Using general procedure C, 3-hydroxy-4-phenyl-cyclopent-2-enone (Lit. 17) was reacted with benzaldehyde and N-[2-(1H-indol-3-yl)-ethyl]-acetamide to give the title compound as a pink solid. MS: 465.0 ([M+H]$^+$).

EXAMPLE 43

N-(2-{6-Fluoro-2-[(2-hydroxy-5-oxo-3-phenyl-cyclopent-1-enyl)-phenyl-methyl]-1H-indol-3-yl}-ethyl)-acetamide

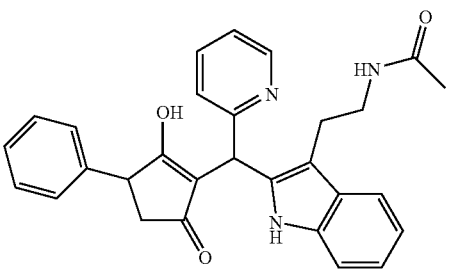

Using general procedure C, 3-hydroxy-4-phenyl-cyclopent-2-enone (Lit. 17) was reacted with benzaldehyde and N-[2-(6-fluoro-1H-indol-3-yl)-ethyl]-acetamide (Example 18.1.) to give the title compound as a pink solid. MS: 483.5 ([M+H]$^+$).

EXAMPLE 44

N-(2-{2-[(2-Hydroxy-5-oxo-3-phenyl-cyclopent-1-enyl)-pyridin-2-yl-methyl]-1H-indol-3-yl}-ethyl)-acetamide Using general procedure C, 3-hydroxy-4-phenyl-cyclopent-2-enone (Lit. 17) was reacted with pyridine-2-carbaldehyde and N-[2-(1H-indol-3-yl)-ethyl]-acetamide to give the title compound as a white solid. MS: 466.3 ([M+H]$^+$).

EXAMPLE 45

N-(2-{2-[(2-Hydroxy-5-oxo-3-phenyl-cyclopent-1-enyl)-pyridin-3-yl-methyl]-1H-indol-3-yl}-ethyl)-acetamide

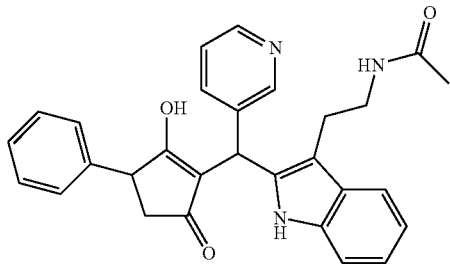

Using general procedure C, 3-hydroxy-4-phenyl-cyclopent-2-enone (Lit. 17) was reacted with pyridine-3-carbaldehyde and N-[2-(1H-indol-3-yl)-ethyl]-acetamide to give the title compound as pale brown solid. MS: 466.3 ([M+H]$^+$).

EXAMPLE 46

N-(2-{2-[(2-Hydroxy-5-oxo-3-phenyl-cyclopent-1-enyl)-(1H-imidazol-4-yl)-methyl]-1H-indol-3-yl}-ethyl)-acetamide

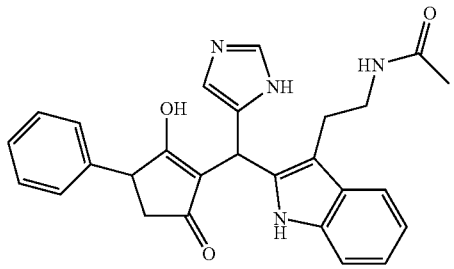

Using general procedure C, 3-hydroxy-4-phenyl-cyclopent-2-enone (Lit. 17) was reacted with 3H-imidazole-4-carbaldehyde and N-[2-(1H-indol-3-yl)-ethyl]-acetamide to give the title compound as pale brown solid. MS: 455.0 ([M+H]$^+$).

EXAMPLE 47

N-(2-{2-[(2-Hydroxy-5-oxo-3-phenyl-cyclopent-1-enyl)-(1H-imidazol-2-yl)-methyl]-1H-indol-3-yl}-ethyl)-acetamide

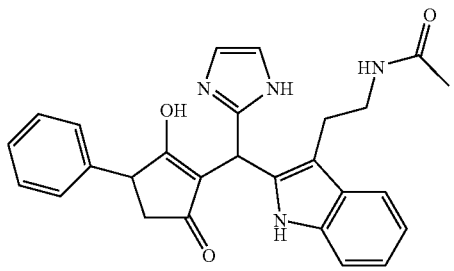

Using general procedure C, 3-hydroxy-4-phenyl-cyclopent-2-enone (Lit. 17) was reacted with 1H-imidazole-2-carbaldehyde and N-[2-(1H-indol-3-yl)-ethyl]-acetamide to give the title compound as pale brown solid. MS: 455.0 ([M+H]$^+$).

EXAMPLE 48

N-(2-{5-Ethyl-2-[(2-hydroxy-5-oxo-3-phenyl-cyclopent-1-enyl)-phenyl-methyl]-1H-indol-3-yl}-ethyl)-acetamide

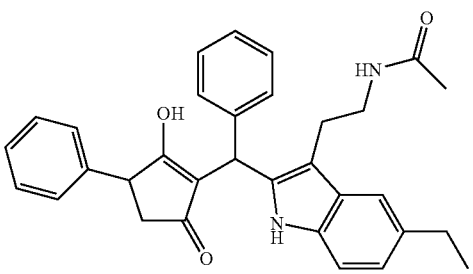

Using general procedure C, 3-hydroxy-4-phenyl-cyclopent-2-enone (Lit. 17) was reacted with benzaldehyde and N-[2-(5-ethyl-1H-indol-3-yl)-ethyl]-acetamide (Lit. 6) to give the title compound as an orange solid. MS: 493.4 ([M+H]$^+$).

EXAMPLE 49

2-{[3-(2-Amino-ethyl)-5-methyl-1H-indol-2-yl]-phenyl-methyl}-3-hydroxy-4-phenyl-cyclopent-2-enone

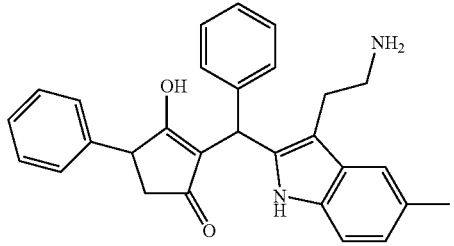

Using general procedure C, 3-hydroxy-4-phenyl-cyclopent-2-enone (Lit. 17) was reacted with benzaldehyde and 2-(5-ethyl-1H-indol-3-yl)-ethylamine to give the title compound as orange solid. MS: 437.1 ([M+H]$^+$).

EXAMPLE 50

N-(2-{2-[(2-Hydroxy-5-oxo-3-phenyl-cyclopent-1-enyl)-phenyl-methyl]-5-methyl-1H-indol-3-yl}-ethyl)-acetamide

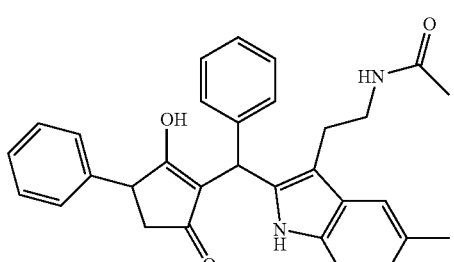

Using general procedure C, 3-hydroxy-4-phenyl-cyclopent-2-enone (Lit. 17) was reacted with benzaldehyde and N-[2-(5-methyl-1H-indol-3-yl)-ethyl]-acetamide (Lit. 7) to give the title compound as orange solid. MS: 479.0 ([M+H]+).

EXAMPLE 51

2-{[3-(2-Amino-ethyl)-6-ethyl-1H-indol-2-yl]-phenyl-methyl}-3-hydroxy-4-phenyl-cyclopent-2-enone

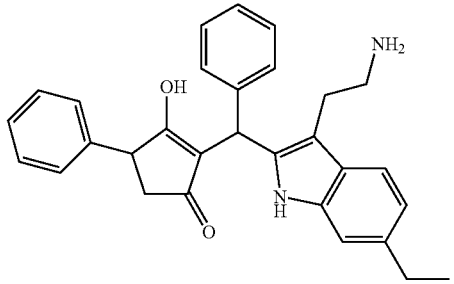

Using general procedure C, 3-hydroxy-4-phenyl-cyclopent-2-enone (Lit. 17) was reacted with benzaldehyde and 2-(6-ethyl-1H-indol-3-yl)-ethylamine (Lit. 8) to give the title compound as a pale brown solid. MS: 451.0 ([M+H]+).

EXAMPLE 52

N-(2-{6-Ethyl-2-[(2-hydroxy-5-oxo-3-phenyl-cyclopent-1-enyl)-phenyl-methyl]-1H-indol-3-yl}-ethyl)-acetamide

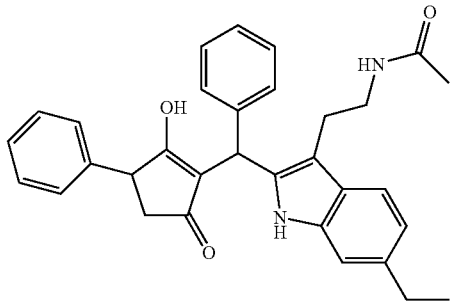

52.1 N-[2-(6-Ethyl-1H-indol-3-yl)-ethyl]-acetamide was prepared from 2-(6-ethyl-1H-indol-3-yl)-ethylamine (Lit. 8) as described in Example 16.1.

52.2. Using general procedure C, 3-hydroxy-4-phenyl-cyclopent-2-enone (Lit. 17) was reacted with benzaldehyde and N-[2-(6-ethyl-1H-indol-3-yl)-ethyl]-acetamide to give N-(2-{6-ethyl-2-[(2-hydroxy-5-oxo-3-phenyl-cyclopent-1-enyl)-phenyl-methyl]-1H-indol-3-yl}-ethyl)-acetamide as a pale brown solid. MS: 493.1 ([M+H]+).

EXAMPLE 53

2-{[3-(2-Amino-2-methyl-propyl)-6-chloro-1H-indol-2-yl]-phenyl-methyl}-3-hydroxy-4-phenyl-cyclopent-2-enone

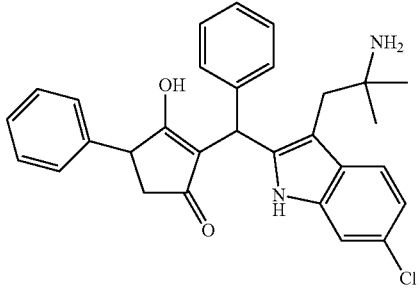

Using general procedure C, 3-hydroxy-4-phenyl-cyclopent-2-enone (Lit. 17) was reacted with benzaldehyde and 2-(6-chloro-1H-indol-3-yl)-1,1-dimethyl-ethylamine (prepared in analogy to Lit. 9) to give the title compound as a pale yellow solid. MS: 485.4 ([M+H]+).

EXAMPLE 54

N-(2-{6-Chloro-2-[(2-hydroxy-5-oxo-3-phenyl-cyclopent-1-enyl)-phenyl-methyl]-1H-indol-3-yl}-1,1-dimethyl-ethyl)-acetamide

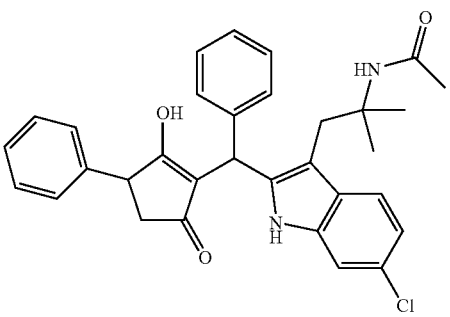

54.1. N-[2-(6-Chloro-1H-indol-3-yl)-1,1-dimethyl-ethyl]-acetamide was prepared from 2-(6-chloro-1H-indol-3-yl)-1,1-dimethyl-ethylamine (prepared in analogy to Lit. 9) by acylation as described in Example 16.1.

54.2. Using general procedure C, 3-hydroxy-4-phenyl-cyclopent-2-enone (Lit. 17) was reacted with benzaldehyde and N-[2-(6-chloro-1H-indol-3-yl)-1,1-dimethyl-ethyl]-acetamide to give N-(2-{6-chloro-2-[(2-hydroxy-5-oxo-3-phenyl-cyclopent-1-enyl)-phenyl-methyl]-1H-indol-3-yl}-1,1-dimethyl-ethyl)-acetamide as a pale yellow solid. MS: 527.3 ([M+H]+).

EXAMPLE 55

N-(2-{6-Chloro-2-[(2-hydroxy-5-oxo-3-phenyl-cyclopent-1-enyl)-phenyl-methyl]-5-methoxy-1H-indol-3-yl}-ethyl)-acetamide

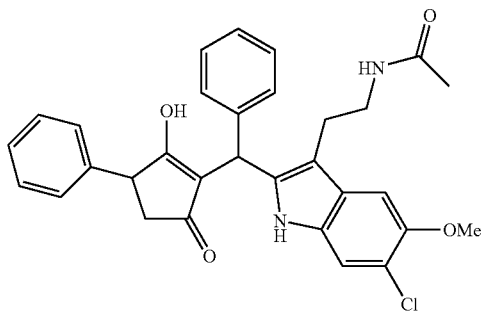

Using general procedure C, 3-hydroxy-4-phenyl-cyclopent-2-enone (Lit. 17) was reacted with benzaldehyde and N-[2-(6-chloro-5-methoxy-1H-indol-3-yl)-ethyl]-acetamide to give the title compound as a pale red solid. MS: 529.3 ([M+H]$^+$).

EXAMPLE 56

N-(2-{2-[(2-Hydroxy-5-oxo-3-phenyl-cyclopent-1-enyl)-phenyl-methyl]-6-methoxy-1H-indol-3-yl}-ethyl)-acetamide

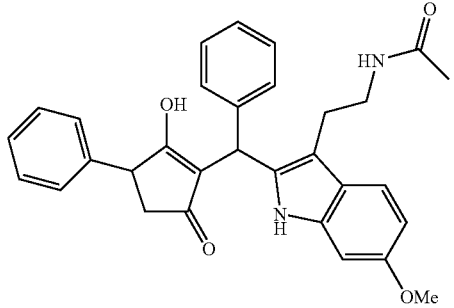

Using general procedure C, 3-hydroxy-4-phenyl-cyclopent-2-enone (Lit. 17) was reacted with benzaldehyde and N-[2-(6-methoxy-1H-indol-3-yl)-ethyl]-acetamide (Lit. 7) to give the title compound as a pale red solid. MS: 495.5 ([M+H]$^+$).

EXAMPLE 57

N-(2-{2-[(2-Hydroxy-5-oxo-3-phenyl-cyclopent-1-enyl)-phenyl-methyl]-5-methoxy-1H-indol-3-yl}-ethyl)-acetamide

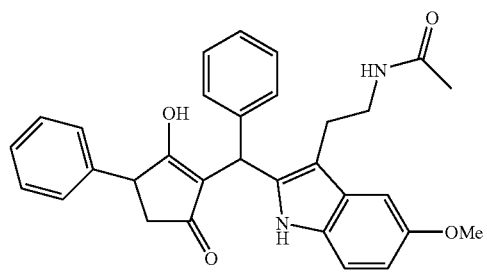

Using general procedure C, 3-hydroxy-4-phenyl-cyclopent-2-enone (Lit. 17) was reacted with benzaldehyde and N-[2-(5-methoxy-1H-indol-3-yl)-ethyl]-acetamide to give the title compound as a pale red solid. MS: 495.4 ([M+H]$^+$).

EXAMPLE 58

3-{[6-Fluoro-3-(2-hydroxy-ethyl)-1H-indol-2-yl]-phenyl-methyl}-4-hydroxy-5-isopropyl-1,5-dihydro-pyrrol-2-one

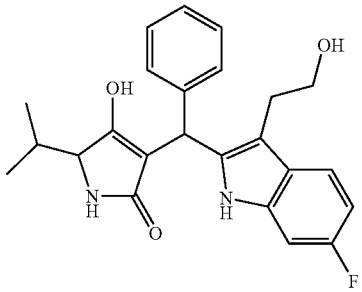

Using general procedure D, rac-4-hydroxy-5-isopropyl-1,5-dihydro-pyrrol-2-one (Lit. 11) was reacted with benzaldehyde and 2-(6-fluoro-1H-indol-3-yl)-ethanol to give the title compound as a pale yellow solid. MS: 409.1 ([M+H]$^+$).

EXAMPLE 59

2-[(5-Fluoro-3-methyl-1H-indol-2-yl)-phenyl-methyl]-1-hydroxy-7a-methyl-5,6,7,7a-tetrahydro-pyrrolizin-3-one

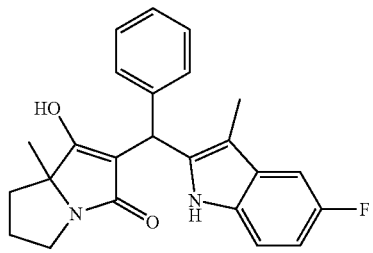

Using general procedure D, rac-1-hydroxy-7a-methyl-5,6,7,7a-tetrahydro-pyrrolizin-3-one (Example C) was reacted with benzaldehyde and 5-fluoro-3-methyl-1H-indole to give the title compound as a red solid. MS: 391.1 ([M+H]$^+$).

EXAMPLE 60

3-[(5-Fluoro-3-methyl-1H-indol-2-yl)-phenyl-methyl]-4-hydroxy-5,5-dimethyl-1,5-dihydro-pyrrol-2-one

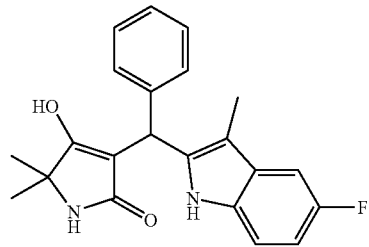

Using general procedure D, rac-4-hydroxy-5,5-dimethyl-1,5-dihydro-pyrrol-2-one (Lit. 18) was reacted with benzaldehyde and 5-fluoro-3-methyl-1H-indole to give the title compound as a yellow solid. MS: 365.1 ([M+H]$^+$).

EXAMPLE 61

(R)-5-Benzyl-3-[(5-fluoro-3-methyl-1H-indol-2-yl)-phenyl-methyl]-4-hydroxy-5-methyl-1,5-dihydro-pyrrol-2-one

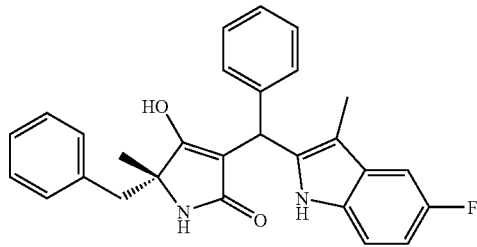

Using general procedure D, (R)-5-benzyl-4-hydroxy-5-methyl-1,5-dihydro-pyrrol-2-one (Example D) was reacted with benzaldehyde and 5-fluoro-3-methyl-1H-indole to give the title compound as a yellow solid. MS: 441.1 ([M+H]$^+$).

EXAMPLE 62

(R)-3-[(5-Fluoro-3-methyl-1H-indol-2-yl)-phenyl-methyl]-4-hydroxy-5-isopropyl-5-methyl-1,5-dihydro-pyrrol-2-one

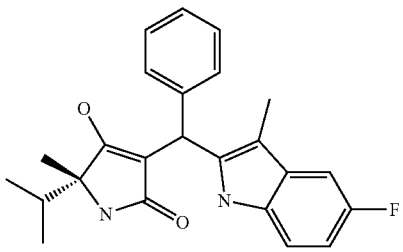

Using general procedure D, (R)-4-hydroxy-5-isopropyl-5-methyl-1,5-dihydro-pyrrol-2-one (Example E) was reacted with benzaldehyde and 5-fluoro-3-methyl-1H-indole to give the title compound as a pale yellow solid. MS: 393.1 ([M+H]$^+$).

EXAMPLE 63

N-{2-[((R)-4-Hydroxy-5-methyl-2-oxo-5-phenyl-2,5-dihydro-1H-pyrrol-3-yl)-phenyl-methyl]-6-methyl-1H-indol-3-ylmethyl}-acetamide

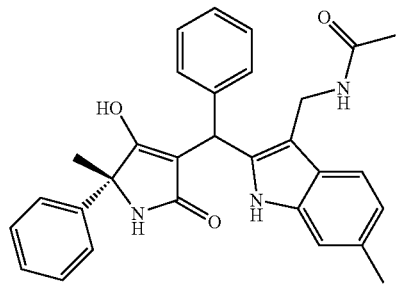

63.1. 6-Methyl-1H-indole-3-carbaldehyde oxime

To a solution of 6-methyl-1H-indole-3-carbaldehyde (0.96 g, Lit. 20) in ethanol (30 ml) was added at 22° C. hydroxylamine hydrochloride (0.46 g) and sodium acetate (0.54 g) and the mixture was stirred for 3 h. The mixture was evaporated and the residue triturated with water and dichloromethane/n-heptane (1:1) and dried to give the title compound (0.96 g) as a pink solid. MS: 175.3 ([M+H]$^+$).

63.2. C-(6-Methyl-1H-indol-3-yl)-methylamine

To a mixture of 6-methyl-1H-indole-3-carbaldehyde oxime (0.66 g) and NiCl$_2$.6 H$_2$O (0.97 g) in methanol (60 ml) was added at 22° C. sodium borohydride (3.04 g) in portions. The suspension was filtered and the filtrate evaporated. The residue was partitioned between aqueous NH$_3$ (1%) and ethyl acetate, the organic layer was dried and evaporated to the give the crude title compound as a yellow semi solid (0.68 g).

63.3. N-(6-Methyl-1H-indol-3-ylmethyl)-acetamide

To a solution of C-(6-methyl-1H-indol-3-yl)-methylamine (0.24 g) in dichloromethane (4 ml) was added acetic anhydride (0.14 ml) and pyridine (0.13 ml) and stirring was continued at 22° C. for 20 min. The mixture was washed with aqueous HCl (1N), the organic layer was dried and evaporated. The residue was chromatographed on silica using dichloromethane/methanol (70:1) to give the title compound as a colorless foam (0.15 g). MS: 203.1 ([M+H]$^+$).

63.4 Using general procedure D, (R)-4-hydroxy-5-methyl-5-phenyl-1,5-dihydro-pyrrol-2-one (Example F) was reacted with benzaldehyde and N-(6-methyl-1H-indol-3-ylmethyl)-acetamide to give the title compound as a white solid. MS: 478.4 ([M–H]$^-$).

EXAMPLE 64

(R)-4-Hydroxy-5-methyl-3-[(3-methyl-1H-indol-2-yl)-phenyl-methyl]-5-phenyl-1,5-dihydro-pyrrol-2-one

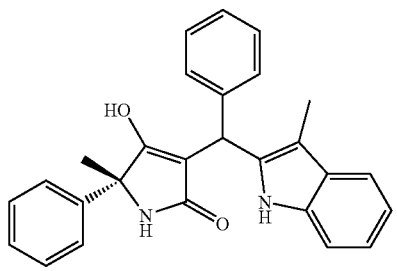

Using general procedure D, (R)-4-hydroxy-5-methyl-5-phenyl-1,5-dihydro-pyrrol-2-one (prepared according to Lit. 11, see also Lit. 19) was reacted with benzaldehyde and 3-methyl-1H-indole to give the title compound as a yellow foam. MS: 409.2 ([M+H]$^+$).

EXAMPLE 65

(R)-3-[(3,5-Dimethyl-1H-indol-2-yl)-phenyl-methyl]-4-hydroxy-5-methyl-5-phenyl-1,5-dihydro-pyrrol-2-one

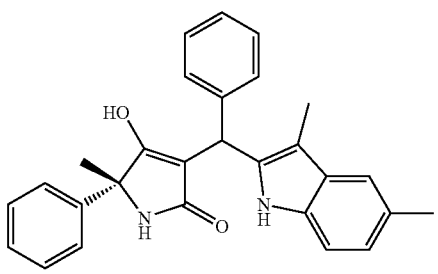

Using general procedure D, (R)-4-hydroxy-5-methyl-5-phenyl-1,5-dihydro-pyrrol-2-one (prepared according to Lit. 11, see also Lit. 19) was reacted with benzaldehyde and 3,5-dimethyl-1H-indole (Lit. 21) to give the title compound as a yellow foam. MS: 423.3 ([M+H]$^+$).

EXAMPLE 66

(R)-3-[(3,6-Dimethyl-1H-indol-2-yl)-phenyl-methyl]-4-hydroxy-5-methyl-5-phenyl-1,5-dihydro-pyrrol-2-one

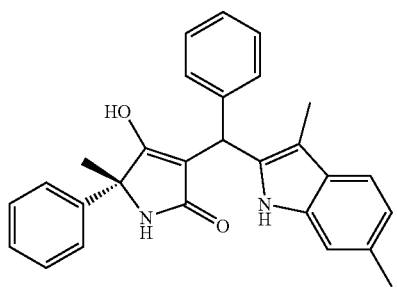

Using general procedure D, (R)-4-hydroxy-5-methyl-5-phenyl-1,5-dihydro-pyrrol-2-one (prepared according to Lit. 11, see also Lit. 19) was reacted with benzaldehyde and 3,6-dimethyl-1H-indole (Lit. 22) to give the title compound as a yellow foam. MS: 423.3 ([M+H]$^+$).

EXAMPLE 67

(R)-3-[(5-Fluoro-3-methyl-1H-indol-2-yl)-phenyl-methyl]-4-hydroxy-5-methyl-5-phenyl-1,5-dihydro-pyrrol-2-one

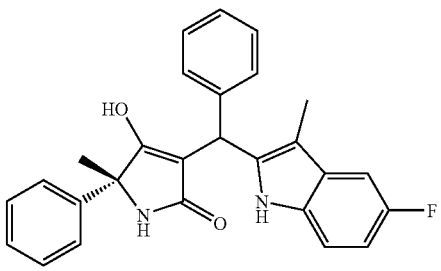

Using general procedure D, (R)-4-hydroxy-5-methyl-5-phenyl-1,5-dihydro-pyrrol-2-one (prepared according to Lit. 11, see also Lit. 19) was reacted with benzaldehyde and 5-fluoro-3-methyl-1H-indole to give the title compound as a pale yellow foam. MS: 425.4 ([M–H]$^-$).

EXAMPLE 68

5-Benzyl-3-[(5-fluoro-3-methyl-1H-indol-2-yl)-thiophen-2-yl-methyl]-4-hydroxy-5H-furan-2-one

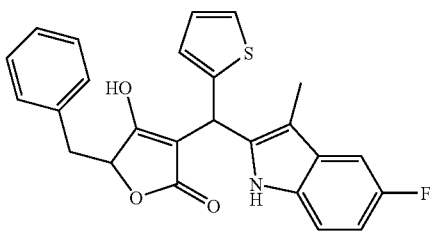

Using general procedure D, rac-5-benzyl-4-hydroxy-5H-furan-2-one (Lit. 13) was reacted with thiophene-2-carbaldehyde and 5-fluoro-3-methyl-1H-indole to give the title compound as a red solid. MS: 434.3 ([M+H]$^+$).

EXAMPLE 69

5-Benzyl-3-[(5-fluoro-3-methyl-1H-indol-2-yl)-thiophen-3-yl-methyl]-4-hydroxy-5H-furan-2-one

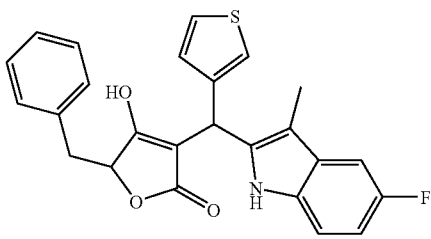

Using general procedure D, rac-5-benzyl-4-hydroxy-5H-furan-2-one (Lit. 13) was reacted with thiophene-3-carbaldehyde and 5-fluoro-3-methyl-1H-indole to give the title compound as a colorless solid. MS: 434.3 ([M+H]$^+$).

EXAMPLE 70

N-(2-{6-Chloro-2-[(4-hydroxy-5-methyl-2-oxo-5-phenyl-2,5-dihydro-furan-3-yl)-phenyl-methyl]-1H-indol-3-yl}-1,1-dimethyl-ethyl)-acetamide

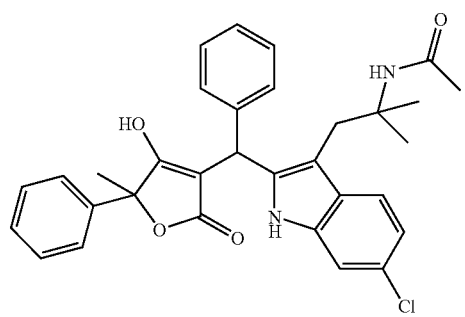

70.1. N-[2-(6-Chloro-1H-indol-3-yl)-1,1-dimethyl-ethyl]-acetamide 2-(6-Chloro-1H-indol-3-yl)-1,1-dimethyl-ethylamine (prepared in analogy to Lit. 9) was acylated as described in Example 63.3 to give the title compound as a brown semi solid.

70.2 Using general procedure D, rac-4-hydroxy-5-methyl-5-phenyl-5H-furan-2-one (prepared according to Example A3) was reacted with benzaldehyde and N-[2-(6-chloro-1H-indol-3-yl)-1,1-dimethyl-ethyl]-acetamide to give the title compound as pale brown solid. MS: 543.3 ([M+H]$^+$).

EXAMPLE 71

N-(2-{5-Chloro-2-[(4-hydroxy-5-methyl-2-oxo-5-phenyl-2,5-dihydro-furan-3-yl)-phenyl-methyl]-1H-indol-3-yl}-1,1-dimethyl-ethyl)-acetamide

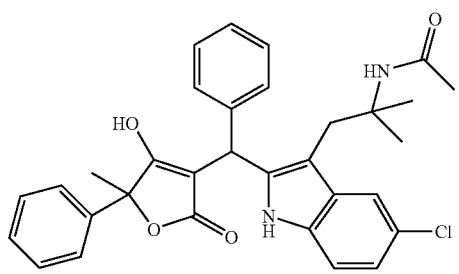

71.1. N-[2-(5-Chloro-1H-indol-3-yl)-1,1-dimethyl-ethyl]-acetamide 2-(5-Chloro-1H-indol-3-yl)-1,1-dimethyl-ethylamine (Lit. 23) was acylated as described in Example 63.3. to give the title compound as a colorless solid. MS: 263.1 ([M−H]$^-$).

71.2. Using general procedure D, rac-4-hydroxy-5-methyl-5-phenyl-5H-furan-2-one (prepared according to Example A3) was reacted with benzaldehyde and N-[2-(5-chloro-1H-indol-3-yl)-1,1-dimethyl-ethyl]-acetamide to give the title compound as pale brown solid. MS: 543.3 ([M+H]$^+$).

EXAMPLE 72

N-{2-[((R)-4-Hydroxy-5-methyl-2-oxo-5-phenyl-2,5-dihydro-furan-3-yl)-phenyl-methyl]-6-methyl-1H-indol-3-ylmethyl}-acetamide

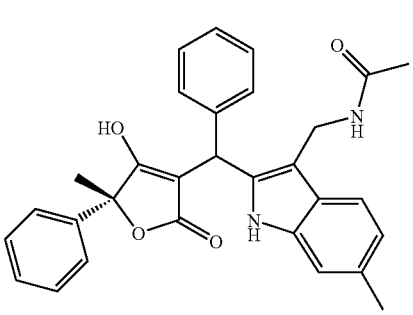

Using general procedure D, (R)-4-hydroxy-5-methyl-5-phenyl-1,5-dihydro-pyrrol-2-one (Example A4) was reacted with benzaldehyde and N-(6-methyl-1H-indol-3-ylmethyl)-acetamide (from Example 63.3) to give the title compound as a yellow solid. MS: 479.4 ([M−H]⁻).

EXAMPLE 73

N-{2-[((S)-4-Hydroxy-5-methyl-2-oxo-5-phenyl-2,5-dihydro-furan-3-yl)-phenyl-methyl]-6-methyl-1H-indol-3-ylmethyl}-acetamide

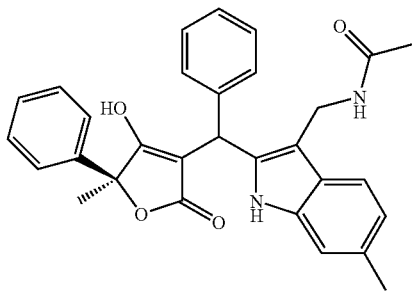

Using general procedure D, (S)-4-hydroxy-5-methyl-5-phenyl-1,5-dihydro-pyrrol-2-one (Example A3) was reacted with benzaldehyde and N-(6-methyl-1H-indol-3-ylmethyl)-acetamide (from Example 63.3) to give the title compound as a yellow solid. MS: 479.4 ([M−H]⁻).

EXAMPLE 74

(R)-4-Hydroxy-5-methyl-3-[(3-methyl-1H-indol-2-yl)-phenyl-methyl]-5-phenyl-5H-furan-2-one

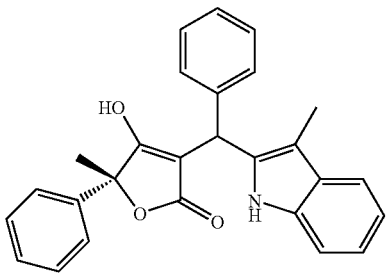

Using general procedure D, (R)-4-hydroxy-5-methyl-5-phenyl-1,5-dihydro-pyrrol-2-one (Example A4) was reacted with benzaldehyde and 3-methyl-1H-indole to give the title compound as a yellow solid. MS: 408.4 ([M−H]⁻).

EXAMPLE 75

(R)-3-[(3,5-Dimethyl-1H-indol-2-yl)-phenyl-methyl]-4-hydroxy-5-methyl-5-phenyl-5H-furan-2-one

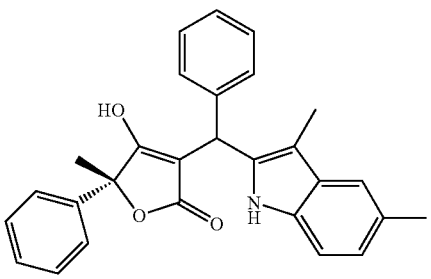

Using general procedure D, (R)-4-hydroxy-5-methyl-5-phenyl-1,5-dihydro-pyrrol-2-one (Example A4) was reacted with benzaldehyde and 3,5-dimethyl-1H-indole (Lit. 21) to give the title compound as a pale brown solid. MS: 422.5 ([M−H]⁻).

EXAMPLE 76

(R)-3-[(3,6-Dimethyl-1H-indol-2-yl)-phenyl-methyl]-4-hydroxy-5-methyl-5-phenyl-5H-furan-2-one

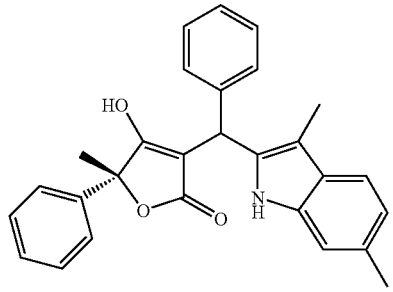

Using general procedure D, (R)-4-hydroxy-5-methyl-5-phenyl-1,5-dihydro-pyrrol-2-one (Example A4) was reacted with benzaldehyde and 3,6-dimethyl-1H-indole (Lit. 22) to give the title compound as a pale brown solid. MS: 422.4 ([M−H]⁻).

EXAMPLE 77

(R)-3-[(5-Fluoro-3-methyl-1H-indol-2-yl)-phenyl-methyl]-4-hydroxy-5-methyl-5-phenyl-5H-furan-2-one

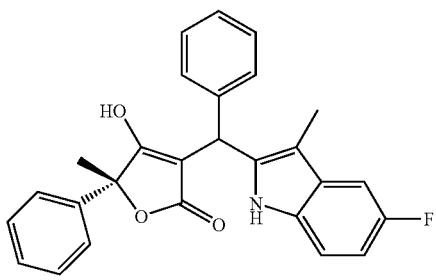

Using general procedure D, (R)-4-hydroxy-5-methyl-5-phenyl-1,5-dihydro-pyrrol-2-one (Example A4) was reacted with benzaldehyde and 5-fluoro-3-methyl-1H-indole to give the title compound as a yellow solid. MS: 426.1 ([M−H]−).

EXAMPLE 78

3-Hydroxy-2-[(3-methyl-1H-indol-2-yl)-phenyl-methyl]-4-phenyl-cyclopent-2-enone

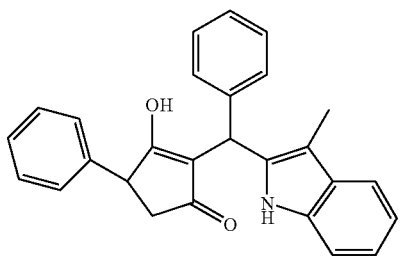

Using general procedure D, rac-3-hydroxy-4-phenyl-cyclopent-2-enone (Lit. 17) was reacted with benzaldehyde and 3-methyl-1H-indole to give the title compound as a red solid. MS: 394.1 ([M+H]+).

EXAMPLE 79

2-[(5-Fluoro-3-methyl-1H-indol-2-yl)-phenyl-methyl]-3-hydroxy-4-phenyl-cyclopent-2-enone

Using general procedure D, rac-3-hydroxy-4-phenyl-cyclopent-2-enone (Lit. 17) was reacted with benzaldehyde and 5-fluoro-3-methyl-1H-indole to give the title compound as a red solid. MS: 412.0 ([M+H]+).

EXAMPLE AA

The inhibition of chymase by the compounds of the present invention can be demonstrated by the peptide substrate assay as described hereinafter.

For the chymase a substrate was chosen containing the 4 amino acid peptide AAPF as a standard substrate for chymotrypsin like compounds (succinyl-Ala-Ala-Pro-Phe-[7-amino-4-methylcoumarin]; Lockhart B E, et al., "Recombinant human mast-cell chymase: an improved procedure for expression in *Pichia pastoris* and purification of the highly active enzyme." *Biotechnol Appl Biochem.* published as immediate publication 26 May 2004 as manuscript BA20040074)). The peptide was synthesized with a purity of 95% from Bachem, Bubendorf, Switzerland). Chymase purified form human skin mast cells was obtained from Calbiochem (Merck Biosciences, San Diego, Calif., USA). The assay buffer was 0.15 M NaCl, 0.05M, Tris HCl, 0.05% CHAPS (3-[(3-Cholamidopropyl)-dimethylammonio]-1-propane sulphonate), 0.1 mg/ml Heparin (Heparin sodium, Sigma, porcine intestinal mucosa), 0.02 mM AAPF-substrate, 1 nM Chymase at pH 7.4. The assay was performed in 96-well plates (Packard Optiplate), with a 0.05 ml volume at room temperature. Chymase activity was indicated by the initial rate of increase in fluorescence at 340/440 nm (excitation/emission) from free 7-amino-4-methylcoumarin released from the substrate. Inhibition of the activity by inhibitory compounds was read after 30 min pre-incubation with the chymase at room temperature in assay buffer without AAPF-substrate. The assay was then started by addition of the indicated concentration of AAPF-substrate.

The IC50 values of the active compounds of the present invention preferably amount to about (1000) to (1) nM, especially about (30) to (1) nM.

| Example | IC50 (nM) |
| --- | --- |
| Example 11 | 13 |
| Example 16 | 24 |
| Example 43 | 3 |
| Example 63 | 10 |
| Example 67 | 5 |
| Example 72 | 15 |
| Example 79 | 2 |

EXAMPLE BB

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |

| -continued | | |
|---|---|---|
| Ingredients | Per tablet | |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

EXAMPLE CC

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE DD

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

EXAMPLE EE

Soft gelatin capsules containing the following ingredients can be manufactured in a conventional manner:

| Capsule contents | |
|---|---|
| Compound of formula (I) | 5.0 mg |
| Yellow wax | 8.0 mg |

| -continued | |
|---|---|
| Capsule contents | |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg |
| | (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

EXAMPLE FF

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:

1. A Compound of formula (I)

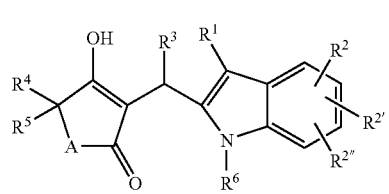

(I)

wherein

A is selected from the group consisting of —$CH_2$—, —O— and —NR'—, wherein R' is selected from the group consisting of hydrogen and $C_{1-6}$ alkyl, or wherein R' and $R^4$ form $C_{2-5}$ alkylene;

$R^1$ is selected from the group consisting of hydrogen, halogen, nitro, cyano, amino, $C_{1-6}$ alkyl, heteroalkyl, $C_{3-7}$ cycloalkyl, $C_{2-6}$ alkenyl, $C_{2-6}$ alkynyl, hydroxy, $C_{1-6}$ alkoxy, —NR'R", —($C_{0-6}$ alkylene)-NR'R", wherein R' and R" are independently selected from the group consisting of hydrogen, $C_{1-6}$ alkyl, heteroalkyl, formyl, $C_{1-6}$ alkylcarbonyl, optionally substituted $C_{3-7}$ cycloalkylcarbonyl, optionally substituted arylcarbonyl, optionally substituted heteroarylcarbonyl, optionally substituted heterocyclylcarbonyl, $C_{1-6}$ alkylsulfonyl, optionally substituted $C_{3-7}$ cycloalkylsulfonyl, optionally substituted arylsulfonyl, optionally substituted heteroarylsulfonyl and optionally substituted heterocyclylsulfonyl, and —($C_{0-6}$ alkylene)-OR', wherein R' is selected from the group consisting of hydrogen, $C_{1-6}$ alkyl, heteroalkyl, formyl and $C_{1-6}$ alkylcarbonyl;

$R^2$, $R^{2'}$ and $R^{2''}$ are independently selected from the group consisting of hydrogen, halogen, cyano, nitro, amino, mono- or di-$C_{1-6}$ alkyl substituted amino, $C_{1-6}$ alkyl, $C_{2-6}$ alkenyl, $C_{2-6}$ alkynyl, heteroalkyl, hydroxy and $C_{1-6}$ alkoxy;

$R^3$ is selected from the group consisting of hydrogen, halogen, cyano, nitro, amino, mono- or di-$C_{1-6}$ alkyl substituted amino, $C_{1-6}$ alky, $C_{2-6}$ alkenyl, $C_{2-6}$ alkynyl, heteroalkyl, hydroxy, $C_{1-6}$ alkoxy, optionally substituted $C_{3-7}$ cycloalkyl, optionally substituted aryl, optionally substituted heteroaryl, optionally substituted heterocyclyl, optionally substituted $C_{3-7}$ cycloalkyl-$C_{1-6}$ alkyl, optionally substituted aryl-$C_{1-6}$ alkyl, optionally substituted heteroaryl-$C_{1-6}$ alkyl and optionally substituted heterocyclyl-$C_{1-6}$ alkyl;

$R^4$ is selected from the group consisting of hydrogen, halogen, cyano, nitro, amino, mono- or di-$C_{1-6}$ alkyl substituted amino, $C_{1-6}$ alkyl, $C_{2-6}$ alkenyl, $C_{2-6}$ alkynyl, heteroalkyl, hydroxy, $C_{1-6}$ alkoxy, optionally substituted $C_{3-7}$ cycloalkyl, optionally substituted aryl, optionally substituted heteroaryl, optionally substituted heterocyclyl, optionally substituted $C_{3-7}$ cycloalkyl-$C_{1-6}$ alkyl, optionally substituted aryl-$C_{1-6}$ alkyl, optionally substituted heteroaryl-$C_{1-6}$ alkyl and optionally substituted heterocyclyl-$C_{1-6}$ alkyl;

$R^5$ is selected from the group consisting of hydrogen and $C_{1-6}$ alkyl; or $R^4$ and $R^5$, together with the carbon atom to which they are attached, form an optionally substituted $C_{3-7}$ cycloalkyl ring or an optionally substituted heterocyclyl ring;

$R^6$ is selected from the group consisting of hydrogen and $C_{1-6}$ alkyl;

or a pharmaceutically acceptable salt thereof.

2. A compound according to claim 1, wherein $R^3$ is selected from the group consisting of $C_{1-6}$ alkyl, optionally substituted aryl, optionally substituted heteroaryl, optionally substituted aryl $C_{1-6}$ alkyl and optionally substituted heteroaryl $C_{1-6}$ alkyl.

3. A compound according to claim 1, wherein $R^3$ is selected from the group consisting of $C_{1-6}$ alkyl, phenyl $C_{1-6}$ alkyl, phenyl optionally substituted by one to three fluorine atoms, and heteroaryl optionally substituted by one to three fluorine atoms, wherein heteroaryl is a monocyclic aromatic radical of 5 or 6 ring atoms, containing one or two ring nitrogen atoms or one ring sulfur atom.

4. A compound according to claim 1, wherein $R^3$ is phenyl.

5. A compound according to claim 1, wherein $R^1$ is selected from the group consisting of $C_{1-6}$ alkyl, —($C_{0-6}$ alkylene)-NR'R", wherein R' and R" are independently selected from the group consisting of hydrogen, $C_{1-6}$ alkylcarbonyl, optionally substituted arylcarbonyl, optionally substituted heteroarylcarbonyl, optionally substituted arylsulfonyl and optionally substituted heteroarylsulfonyl, and —($C_{0-6}$ alkylene)-OR', wherein R' is selected from the group consisting of hydrogen and $C_{1-6}$ alkylcarbonyl.

6. A compound according to claim 1, wherein $R^1$ is selected from the group consisting of $C_{1-6}$ alkyl, —($C_{2-6}$ alkylene)-NR'R", wherein R' and R" are independently selected from the group consisting of hydrogen, acetyl, arylcarbonyl, wherein aryl is optionally substituted by one or two trifluoromethyl groups and arylsulfonyl, and —($C_{2-6}$ alkylene)-OR', wherein R' is selected from the group consisting of hydrogen and acetyl.

7. A compound according to claim 1, wherein $R^1$ is selected from the group consisting of 2-aminoethyl, 2-acetylaminoethyl, 2-acetylamino-2,2-dimethylethyl, methyl, isopropyl and 2-hydroxyethyl.

8. A compound according to claim 1, wherein $R^2$, $R^{2'}$ and $R^{2''}$ are independently selected from the group consisting of hydrogen, halogen, $C_{1-6}$ alkyl and $C_{1-6}$ alkoxy.

9. A compound according to claim 1, wherein two of $R^2$, $R^{2'}$ and $R^{2''}$ are hydrogen, and the other is selected from the group consisting of hydrogen, halogen, $C_{1-6}$ alkyl and $C_{1-6}$ alkoxy.

10. A compound according to claim 1, wherein two of $R^2$, $R^{2'}$ and $R^{2''}$ are hydrogen, and the other is selected from the group consisting of hydrogen, chloro, fluoro, methyl, ethyl or methoxy.

11. A compound according to claim 1, wherein two of $R^2$, $R^{2'}$ and $R^{2''}$ are hydrogen, and the other is at 5 or 6 position of the indole ring and selected from the group consisting of hydrogen, chloro, fluoro, methyl and ethyl.

12. A compound according to claim 1, wherein $R^6$ is hydrogen.

13. A compound according to claim 1, wherein
$R^4$ is selected from the group consisting of hydrogen, $C_{1-6}$ alkyl, optionally substituted $C_{3-7}$ cycloalkyl, optionally substituted aryl, optionally substituted $C_{3-7}$ cycloalkyl $C_{1-6}$ alkyl and optionally substituted aryl $C_{1-6}$ alkyl and
$R^5$ is selected from the group consisting of hydrogen and $C_{1-6}$ alkyl; or
$R^4$ and $R^5$, together with the carbon atom to which they are attached, form an optionally substituted $C_{3-7}$ cycloalkyl ring.

14. A compound according to claim 1, wherein A is —$CH_2$—.

15. A compound according to claim 1, wherein A is —$CH_2$—, $R^4$ is phenyl and $R^5$ is hydrogen.

16. A compound according to claim 1, wherein A is —NR'—, wherein R' is selected from the group consisting of hydrogen and $C_{1-6}$ alkyl.

17. A compound according to claim 1, wherein A is —NR'—, wherein R' is selected from the group consisting of hydrogen and methyl, $R^4$ is isopropyl and $R^5$ is hydrogen.

18. A compound according to claim 1, wherein A is —O—.

19. A compound according to claim 1, wherein A is —O—, $R^4$ is selected from the group consisting of hydrogen, phenyl, $C_{1-6}$ alkyl, optionally substituted $C_{3-7}$ cycloalkyl $C_{1-6}$ alkyl and optionally substituted aryl $C_{1-6}$ alkyl, and $R^5$ is selected from the group consisting of hydrogen and $C_{1-6}$ alkyl; or
$R^4$ and $R^5$, together with the carbon atom to which they are attached, form an optionally substituted $C_{3-7}$ cycloalkyl ring.

20. A compound according to claim 1, wherein A is —O—, $R^4$ is selected from the group consisting of phenyl, benzyl, isobutyl, 2-cyclohexylethyl and phenethyl and $R^5$ is selected from the group consisting of hydrogen and methyl.

21. A compound according to claim 1 selected from the group consisting of
3-[(5-Fluoro-3-methyl-1H-indol-2-yl)-phenyl-methyl]-4-hydroxy-5-isopropyl-1,5-dihydro-pyrrol-2-one,
3-[(5-Fluoro-3-methyl-1H-indol-2-yl)-phenyl-methyl]-4-hydroxy-5-isopropyl-1-methyl-1,5-dihydro-pyrrol-2-one,
4-Hydroxy-5-isopropyl-3-[(3-methyl-1H-indol-2-yl)-phenyl-methyl]-1,5-dihydro-pyrrol-2-one, 3-[(5-Fluoro-3-isopropyl-1H-indol-2-yl)-phenyl-methyl]-4-hydroxy-5-isopropyl-1,5-dihydro-pyrrol-2-one,
N-(2-{2-[(5-Benzyl-4-hydroxy-2-oxo-2,5-dihydro-furan-3-yl)-phenyl-methyl]-6-fluoro-1H-indol-3-yl}-ethyl)-acetamide,
5-Benzyl-3-{[6-fluoro-3-(2-hydroxy-ethyl)-1H-indol-2-yl]-phenyl-methyl}-4-hydroxy-5H-furan-2-one,
3-{[3-(2-Amino-ethyl)-6-fluoro-1H-indol-2-yl]-phenyl-methyl}-5-benzyl-4-hydroxy-5H-furan-2-one; salt with acetic acid,
5-Benzyl-3-[(5-fluoro-3-methyl-1H-indol-2-yl)-phenyl-methyl]-4-hydroxy-5H-furan-2-one,
(2-{6-Fluoro-2-[(4-hydroxy-5-methyl-2-oxo-5-phenyl-2,5-dihydro-furan-3-yl)-phenyl-methyl]-indol-3-yl}-ethyl)-acetamide,
(2-{2-[(4-Hydroxy-5-isobutyl-2-oxo-2,5-dihydro-furan-3-yl)-phenyl-methyl]-indol-3-yl}-ethyl)-acetamide,
N-[2-(2-{[5-(2-Cyclohexyl-ethyl)-4-hydroxy-2-oxo-2,5-dihydro-furan-3-yl]-phenyl-methyl}-6-fluoro-1H-indol-3-yl)-ethyl]-acetamide,
N-(2-{6-Fluoro-2-[(4-hydroxy-2-oxo-5-phenethyl-2,5-dihydro-furan-3-yl)-phenyl-methyl]-1H-indol-3-yl}-ethyl)-acetamide,
N-(2-{2-[(2-Hydroxy-5-oxo-3-phenyl-cyclopent-1-enyl)-phenyl-methyl]-1H-indol-3-yl}-ethyl)-acetamide,
N-(2-{6-Fluoro-2-[(2-hydroxy-5-oxo-3-phenyl-cyclopent-1-enyl)-phenyl-methyl]-1H-indol-3-yl}-ethyl)-acetamide,
N-(2-{5-Ethyl-2-[(2-hydroxy-5-oxo-3-phenyl-cyclopent-1-enyl)-phenyl-methyl]-1H-indol-3-yl}-ethyl)-acetamide,
N-(2-{2-[(2-Hydroxy-5-oxo-3-phenyl-cyclopent-1-enyl)-phenyl-methyl]-5-methyl-1H-indol-3-yl}-ethyl)-acetamide,
2-{[3-(2-Amino-ethyl)-6-ethyl-1H-indol-2-yl]-phenyl-methyl}-3-hydroxy-4-phenyl-cyclopent-2-enone, and,
N-(2-{6-Chloro-2-[(2-hydroxy-5-oxo-3-phenyl-cyclopent-1-enyl)-phenyl-methyl]-1H-indol-3-yl}-1,1-dimethyl-ethyl)-acetamide,
or a pharmaceutically acceptable salt thereof.

22. A process for the manufacture of a compound of Formula (I) as defined in claim 1, comprising the step of coupling of a compound of Formula (III)

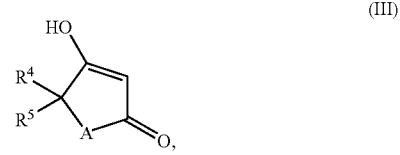

a compound of Formula (IV)

and a compound of Formula (V)

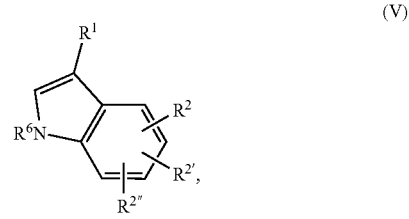

wherein A, $R^1$, $R^2$, $R^{2'}$, $R^{2''}$, $R^3$, $R^4$, $R^5$ and $R^6$ are as defined in claim 1.

23. A pharmaceutical composition comprising a compound according to claim 1 and a pharmaceutically acceptable excipient.

* * * * *